(12) United States Patent
Kaplan et al.

(10) Patent No.: US 6,320,101 B1
(45) Date of Patent: Nov. 20, 2001

(54) ENHANCING INORGANIC CARBON FIXATION BY PHOTOSYNTHETIC ORGANISMS

(75) Inventors: Aaron Kaplan; Judy Lieman-Hurwitz; Daniella Schatz; Ron Mittler, all of Jerusalem; Michal Ronen-Tarazi, Shoham; David J. Bonfil, Meitar, all of (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/332,041

(22) Filed: Jun. 14, 1999

(51) Int. Cl.[7] .............................. A01H 5/00; C12N 15/00; C12N 15/31; C12N 15/63; C12N 15/82
(52) U.S. Cl. .................... 800/284; 800/287; 800/288; 800/291; 800/292; 800/293; 800/294; 800/298; 800/317.3; 800/317.4; 800/312; 800/317.2; 800/307; 800/314; 800/320.3; 800/320.2; 800/320; 800/320.1; 536/23.7; 536/24.1; 435/69.8; 435/411; 435/412; 435/414; 435/415; 435/417; 435/419; 435/468; 435/469; 435/470
(58) Field of Search .................................. 800/278, 284, 800/287, 288, 298, 317.3, 317.4, 312, 317.2, 307, 314, 320.3, 320.2, 320, 320.1; 536/23.7, 24.1; 435/419, 411, 412, 414, 415, 417

(56) References Cited

PUBLICATIONS

Bonfil, D.J. et al., Accession #U62616, GenEmbl, Jul. 1, 1996.*
Omata, T. et al., "Indentification of an ATP–binding cassette transporter involved in bicarbonate uptake in the cyanobacterium Synechococcus sp. strain PCC 7942.", 1999, PNAS, vol. 96, pp. 13571–13576.*
Fukuzawa et al, "A Gene Homologous to Chloroplast Carbonic Anhydrase (icfA) is Essential to Photosynthetic Carbon Fixation in the Cyanobacterium, *Synechococcus* sp. PCC7942", *Proc. Natl. Acad. Sci.*, USA, 89: 4437–4441, 1992.
Bonfil et al, "A Putative $HCO_3$ Transporter in the Cyanobacterium, *Synechococcus* sp. Strain PCC7942", FEBS Letters, 430: 236–240, 1998.
Badger et al, "The $CO_2$ Concentrating Mechanism in Cyanobacteria and Microalgae", *Physiol. Plant.*, 84: 606–615, 1992.
Marco et al, "Inactivation of ndhB encoding subunit II of NADH dehydrogenase in *Synechococcus* sp. PCC7942 resulted in high–$CO_2$ –requiring mutant defective in photosynthetic electron transport following exposure to low $CO_2$", *Plant Physiol.*, 101: 1047–1053, 1993.
Kaplan et al, "Physiological and Molecular Aspects of the Inorganic Carbon–concentrating Mechanism in Cyanobacteria", *Plant Physiol.*, 97: 851–855, 1991.

Ronen–Tarazi et al, "A Mutant of *Synechococcus* sp. PCC7942 Impaired in $HCO_3$ Uptake", *FEMS Micribiol. Lett.* 159: 317–324, 1998.
Yu et al, "Characterization of $CO_2$ and $HCO_3$ Uptake During Steady–State Photosynthesis in the Cyanobacterium, *Synechococcus* sp. PCC7942", *Aust. J. Plant Physiol.*, 21: 185–195, 1994.
Kaplan et al, Inorganic Carbon Uptake by Cynobacteria, in Methods in Enzymology (Packer L. Amd Glazer, A.N. Eds.) pp 534–539, Academic Press, New York, 1988.
Sultemeyer et al, "PsaE–and NdhF–Mediated Electron Transport Affect Bicarbonate Transport Rather Than Carbon Dioxide Uptake in the Cyanobacterium, *Synechococcus* sp. PCC7942", *Planta*, 201: 36–42, 1997.
Tchernov et al, "Sustained Net $CO_2$ Evolution During Photosynthesis by Mairne Microorganisms", *Curr. Biol.*, 7: 723–728, 1997.
Marcus et al, "High $CO_2$ Requiring Mutant of *Anacystis Nidulans* $R_2$", Plant Physiol., 82: 610–612, 1986.
Omata et al, "Biosynthesis of a 42–kD Polypeptide in the Cytoplasmic Membrane of the Cyanobacterium *Anacystis Nidulans* Strain $R_2$ During Adaption Low $CO_2$ Concentration", *Plant Physiol.*, 80: 525–530, 1986.
Kaplan et al, "The $CO_2$ Concentrating Mechanism of Cyanobacteria: Physiological Molecular and Theoretical Studies", Spec. Issue of Botanical Magazine vol. 2, pp 53–21, Tokyo, 1990.
Sultemeyer et al, "Fast Induction of High–Affinity $HCO_3$ Transport in Cyanobacteria", *Plant Physiol*, 116: 183–192, 1998.
Omata, T., "Characterization of the Downstream Region of cmpA: Identification of a Gene Cluster Encoding a Putative Permease of the Cyanobacterium *Synechococcus* PCC7942", in Research in Photosynthesis (Murata N. Ed) vol. III, 807–810, Kluwer Academ. Pub., The Netherlands, 1992.
Kaplan et al, "The Inorganic Carbon–Concentrating Mechanism in Cyanobacteria: Induction and Ecological Significance", *Can. J. Bot.*, Sp. Issue, pp 917–924, 1998.
Ronen–Tarizi et al, "Response of Photosynthetic Microorganisms to Changing Ambient Concentration of $CO_2$ ", *Molecular Ecology of Aquatic Microbes* (Joint I Ed.), pp 323–334, 1995.

(List continued on next page.)

Primary Examiner—David T. Fox
Assistant Examiner—Anne R Kubelik

(57) ABSTRACT

A method of enhancing inorganic carbon fixation by a photosynthetic organism. The method is effected by transforming cells of the photosynthetic organism with an expressible polynucleotide encoding a polypeptide having a bicarbonate transporter activity. Preferably, the polynucleotide further includes a plant promoter. Sequences and constructs for implementing the method are also described.

23 Claims, 7 Drawing Sheets

OTHER PUBLICATIONS

Lieman–Hurwitz et al, "Molecular Analysis of High $CO_2$ Requiring Mutants: Involvement of Genes in the Region of rbc, including rbcS, in the ability of Cyanobacteria to Grow Under Low $CO_2$", Proc. 2nd Intl Symposium on Inorganic Carbon Uptake by Aquatic Photosynthetic Organisms, (Coleman B. Ed.) *Can J Bot*, 69: 945–950, 1990.

Schwarz et al, "Is There a Role for the 42 Kilodalton Polypeptide in Inorganic Carbon Uptake bt Cyanobacteria?", *Plant Physiol.*, 88: 284–288, 1988.

Omata et al, "Sequencing and Modification of the Gene Encoding the 42–Kilodalton Protein in the Cytoplamic Membrane of Synechococcus PCC7942", *Plant Physiol*, 93: 305–311, 1990.

Ronen–Tarizi et al, "The Genomic Region of rbcLS in *Synechococcus* sp PCC7942 Contains Genes Invloved in the Ability to Grow Under Low $CO_2$ Concentration and in Chlorophyll Biosynthesis", *Plant Physiol*, 108: 1461–1469, 1995.

Schwarz et al, "Low Activiation State of Ribulose–1,5–Biphosphate Carboxylase/Oxygenase in Carboxysome–Defective *Synechococcus* Mutants", *Plant Physiol*, 108: 183–190, 1995.

Tyrrell et al, "Ethoxyzolamide Differentially Inhibits $CO_2$ Uptake and $Na^+$–Independent and $NA^+$—Dependent $HCO_3$ Uptake in the Cyanobacterium Synechococcus sp PCC7942", *Plant Physiol*, 112: 79–88, 1996.

Ohkawa et al, "The use of Mutants in the Analysis of the $CO_2$ Concentrating Mechanism in Cyanobacteria", *Can J. Bot.*, 76: 1035–1042, 1998.

Kaplan et al, "Physiological and Molecular Studies on the Response of Cyanobacteria to Changes in the Ambient Inorganic Carbon Concentration", in *Molec. Biol. Of the Cyanobacteria* (Bryant D. Ed) pp 469–485, Kluwer Acad. Pub., Dordrecht, The Netherlands, 1994.

Badger et al, "The role of Carbonic Anhydrase in Photosynthesis", *Ann. Rev. Plant Physiol. Plant Mol. Biol.*, 45: 369–392, 1994.

Dolganov et al, "Insertional Inactivation of Genes to Isolate Mutants of Synechococcus sp PCC7942: Isolation of Filamentous Strains", J. Bacter., 175: 7644–7651, 1993.

\* cited by examiner

```
ICTB :   1  ATGACTGTCTGGCAAACTCTGACTTTTGCCCATTACCAACCCAACAGTGGGGCCACAGC  60  (SEQ ID NO:2)
            || || |||||| | ||| ||||   || |   || || ||||||| | |||||||     
SLR  :  13  ATCTCTATCTGGCGATCGCTGATGTTTGGCGGTTTTCCCCCCAGGAATGGGGCCGGGGC  72  (SEQ ID NO:4)

ICTB :  61  AGTTTCTTGCATCGGCTGTTTGGCAGCCTGC-GAGCTTGGCGGCCTCCAGCCAGCTGTT  119
            |||  | ||||| |    ||| ||| ||    ||||| |||| | | |||| ||||| 
SLR  :  73  AGTGTGCTCCATCGTTGTTGGCTGGGCTGGGGACAGAG-TTGGATACAGGCTAGTGTGCTCTG  131

ICTB : 120  GGTTTGGTCTGAGGCACTGGGT--GGCTTCTTGCTTGCTGTCGTTCGGCTCCG  177
            | ||||||||||||  ||||| |    |||||| |  ||  | |||||||||
SLR  : 132  GCCCCACTTCGAGGCATTGGGTACGGCT-CTAG-TGGCAATAATTTTATTGCGGCTCCC  189

ICTB : 178  TTTGTGCCCAGTTCCGCCCCTAGGGTTGGGCTAGCCGCGATCGCG-GCCTATTGGGCCCT  236
            ||  |   |    | |||  | | ||||||||     |   ||| |||| ||||||  |
SLR  : 190  TTCACCTCCACCACCATGTTGGGCATTTTTAT-GCTGCTCTGTGGAGCCTTTTGGGCTCT  248

ICTB : 237  GCTCTCGCTGACAGATATCGATTCGCGGCAAGCA---ACCCCCATTCACTGGCTGGTGCT  293
            ||| |    | |    | |  |     ||| |     ||| || ||   |||  |||| 
SLR  : 249  GCTGACCTTTGCTGAT--CAACCAG-GGAAGGGTTTGACTCCCATCCATGTTTTAGTTTT  305

ICTB : 294  GCTCTACTGGGGCGTCGATGCCCTAGCAACGGGACTCTCACCCGTACGGCGCTGCAGCTTT  353
             ||||| |||||  |   ||| || |   || ||||    || | | |||  | |||| 
SLR  : 306  TGCCTACTGGTGCATTCGGCGATCGCCGTGGGATTTTCTCCGGTAAAAATGGCGGGCGGC  365

ICTB : 354  AGTTGGGCTAGCCAAACTGAC-GCTC-TACCTGTGTTGGTTTTTGCCCTAGGCTCGGGTT  411
             ||||||||| |  |||  |  |||  |||||| |||| ||| | |||  |||||| | 
SLR  : 366  GTCGGGGTTAGCGAAATTAACAGCTAATTTATGTCTGTTTCTAC--TGGCGGCGAGGTTA  423

ICTB : 412  CTCCGCAATCCCCGTCTGC-GATCGCTGCTGTTCTCGGTCGTCGTGATCACATCGCTTTT  470
            | |      |||  | ||  ||| |  || ||  |||  |||  |  ||| | ||| ||
SLR  : 424  TTGCAAAACAAATGGTTGAAC-CGGTTAGTAACCGTTGTTTTACTGGTAGGGCTATT  482
```

```
ICTB : 471  TGTCAGTGTCTACGGCCTCAACCAATGGATCTACGGGCGTTGAAGAGCTGGGCGACTTGGGT 530
              ||  ||||| || ||  ||  |  ||||| || ||||  || || ||   |||||||
SLR  : 483  GGTGGGGAGTTACGTCTGCGACAACAGGTGGACGGGGTAGAACAGTTAGCCACTTGGAA  542

ICTB : 531  GGATCGCAACTCGGTTGCCGACTTCACCTCACGGGTTTACAGCTATCTGGGCAACCCCAA  590
            ||||| || ||  ||     ||   |||  ||||| |||| ||| || ||||  || ||
SLR  : 543  TGACCCCACCTCTACCTTGGCCCCAGCCACTAGGGTATATAGCTTTTTAGGTAATCCCAA  602

ICTB : 591  CCTGCTGGCTGCTTATCTGGTGCCGAGCGACTGCCTTT-CTGCAGCAGCGATCGGGGTGT  649
            || || ||||| |||| ||||||||  |  |||  | |   ||||||||  || ||||
SLR  : 603  TCTCTTGGCGGCTTACCTGTGCCCATGACGGGGTTTGAGT-GCCCTGGTGGTAT  661

ICTB : 650  GGGCGGCTGGCTCCCAAGCTGCTGGCGATCG-CTGCGACAGGTGCGAGCAGCTTATGT  708
            ||||  ||| ||    |   ||| |   || ||| ||  ||  || ||||| ||  ||
SLR  : 662  GGCGACGGTGGTGGCCCAAACTGCTGG-GAGCAACCATGTGATTGTTAACCTACTCTGT  720

ICTB : 709  CTGATCCTCACCTACAGTCGCGGTGGCTGGGTTTGTCGCCATGATTTTTGTCTGG  768
              |||  ||  |||   || ||||| ||  |  || ||||   |    |||
SLR  : 721  CTCTTTTTTACCCAGAGCCGGGGCGGTTGGCTAGCAGTGCTGGCCCTGGGAGCTACCTTC  780

ICTB : 769  GCGTTATTAGGCTCTACTGGTTTCAACCCCGTCTACCCGCACCCTGGCGACGCTGGCTA  828
            ||| |  ||||  || |  || ||||   || |  ||||  ||| |||  |||| |
SLR  : 781  CTGGCCCCTTTGTGTACTTCTGGTGTTACCCCAATTACCCAAATTTTGGCAACGGTGGTCT  840

ICTB : 829  TTCCCAGTCGTATTGGGTGGACTAGTCGCGGTGCTCTT-GGTGGCGGTGCTTGGACT---  884
            ||||| |||||  | |||| || |||||||||| | | ||||||||| || ||||
SLR  : 841  TTGCCCCCTGGC----GATCGCC--GTGGCGGTTATATTAGGTGGGGAGCGTTGATTGCG  894

ICTB : 885  -TG-AGCCGTTGCGCGTGCGCGTGTTGAGCATCTTTGTGGGCGTGAAGACAGCAGCAAC  942
             || ||||| ||  || ||||  || |||||   |||| ||||| ||||||||||
SLR  : 895  GTGGAACCGATTCGACTCAGGGCCATGAGCAGCATTTTGCTGGGCGGGAAGACAGCAGTAAT  954
```

```
ICTB :  943 AACTTCCGGATCAATGTCTGGCTGGCGGTGCTGCAGATGATTCAAGATCGGCCTTGGCTG 1002
             ||||||||||||||| |||  |||    |||    ||||| || || ||| || |||
SLR  :  955 AATTTCCGCATCAATGTTTGGGAAGGGGTAAAAGCCATGATCCGAGCCCGCCTATCATT 1014

ICTB : 1003 GGCATCGGCCCCGGCAATACGGCCTTTAACCTGGTTTATCCCCTCTATCAACAGGCGC  1062
             |||||||||  ||   || ||||||||  ||  ||||||||| |||| |  |||| |
SLR  : 1015 GGCATTGGCCCCAGGTAACGAAGCCTTAACCAAATTTATCCTTACTATATGCGGCCCGC 1074

ICTB : 1063 TTTACGGGCGTTGAGCGCCTACTCCGTCCCGTGAAGTCGCGGTTGAGGGCGGACTACTG 1122
             ||  |  |||||||||| ||||| ||  || ||  || |   |||||||     |||
SLR  : 1075 TTCACCGCCCCTGAGTGCCTATTCCATTTACCTAGAAATTTGGTGGAAACGGGTGTAGTT 1134

ICTB : 1123 GGCTTGA-CGGCCTTCGCTTGGCTGCT-GCTGGTCACGGGCGGTGACGGCGGTGCGGCAGG 1180
             ||||| |    ||| || ||| |||| |||    ||| | |||||   || | |||
SLR  : 1135 GGTTTTACCTGTATGCTC-TGGCTGTTGGCCCGTTACCCTAGGCAAAGGC-GTAGAACTGG 1192

ICTB : 1181 TGAGCCGACTTGCGCGGCGATCGCAATCCCC--AAGCCTTTTGTTGATGGCTAGCTTGGC 1238
             | |    | ||  | || ||| ||  |    ||||||  || | ||| ||| |||||
SLR  : 1193 TTAAACG-CTGTCGC-CAAACCCTCGCCGGAAGGCATCTGGATTATGGGGCTTTAGC 1250

ICTB : 1239 CGGTTTGGCAGGAATGCTGGGTCACGGTCTGTGTTGATACCGTGTCTCTATCGACCGAAGC 1298
             | ||| |||  |||  ||||||| ||||| ||||| |||    ||||| ||| | |
SLR  : 1251 GGCGATCATCGGTTTGTTGGTCCACGGATGTAGATACAGTCTGTACCGTCCCCCGGT 1310

ICTB : 1299 CAGTACGCTCTGGTGGCTCTGTATTGG--AGCGATCGCGAGTTTCTGG--CAGC-CCCAA 1353
             |  |  |||  || ||  ||| | ||   |||||  |||  |||||     |  |||
SLR  : 1311 GAGCACTTTGTGGTGG--TTGCTAGTGGCCATTG-TTGCTAGTCAGTGGGCCAGCGCCCAG 1368

ICTB : 1354 CCTTCCAAGCAACTCCCTCCAGAAGCCGAGCATTCAGACGAA 1395
             |   |   |  ||||     |||| ||||    ||   |||
SLR  : 1369 GCCCGTTTGGAGGCCAGTAAAGAA---GAAAATGAGGACAAA 1407
```

Fig. 2 (Continued)

```
SLR   :   5    +++W++L  F  +  PQ+WG  S LHRL  G   ++W  +S L   EALG  L+A+++  +APF
               ISIWRSLMFGGFSPQEWGRGSVLHRLVGWGQSWIQASVLWPHFEALGTALVAIIFIAAPF    64

ICTB  :  61    VPSSALGLGLAAIAAYWALLSLTDIDLRQATPIHWLVLLYMGVDALATGLSPVRAAALVG   120
               ++ LG+  +    A+WALL+  D  +  TPIH LV  YW +  A+A G SPV+ AA   G
SLR   :  65    TSTTMLGIFMLLCGAFWALLTFADQPGKGLTPIHVLVFAYWCISAIAVGFSPVKMAAASG   124

ICTB  : 121    LAKLTLYLLVFALAARVLRNPRLRSLLFSVVITSLFVSVYGLNQWIYGVEELATWVDRN    180
               LAKLT  L +F LAAR+L+N +  + L +VV++  +  L V  YGL Q + GVE+LATW  D
SLR   : 125    LAKLTANLCLFLLAARLLQNKQWLNRLVTVVLLVGLLVGSYGLRQQVDGVEQLATWNDPT   184

ICTB  : 181    SVADFTSRVYSYLGNPNLLAAYLVPTTAFSAAAIGVWRGWLPKLLAIAATGASSLCLILT   240
                 +RVYS+LGNPNLLAAYLVP  T  S  +A+ VWR W PKLL         + LCL  T
SLR   : 185    STLAQATRVYSFLGNPNLLAAYLVPMTGLSLSALVVWRRWPKLLGATWVIVNLLCLFFT   244

ICTB  : 241    YSRGGWLGFVAMIFVWALLGLYWFQPRLPAPWRRWLFPPVLGGLVAVLLVAVLGLEPLRV   300
               +SRGGWL  +A+   +   L   +W+ P+LP  W+RW  P+ +    V +    A++  +EP+R+
SLR   : 245    QSRGGWLAVLAVLALGATFPLALCYFWQLPKFWQRNSLPLAIAVAVILGGGALIAVEPIRL   304

ICTB  : 301    RVLSIFVGREDSSNNFRINVWLAVLQMIQDREWLGIGPGNTAFNLVYPLYQQARFTALSA   360
               R +SIF GREDSSNNFRINVW  V  MI+ RP +GIGPGN AFN +YP Y + RFTALSA
SLR   : 305    RAMSIFAGREDSSNNFRINVWEGVKAMIRARPIIGIGPGNEAFNQIYPYYMRPRFTALSA   364

ICTB  : 361    YSVPLEVAVEGGLLGLTAFAWLLLVTAVTAVRQVSRLRRDRNPQAFWLMASIAGLAGMLG   420
               YS+  LE+ VE G++G T    WLL VT    V  V R R+   P+  W+M +LA + G+L
SLR   : 365    YSIYLEILVETGVVGFTCMLWLLAVTLGKGVELVKRCRQTLAPEGIWIMGALAAIIGLLV   424

ICTB  : 421    HGLFDTVLYRPBASTLNWLCIGAIASFWQPQPSKQLPPEAEHSDEKM   467
               HG+ DTV YRP STLWWL +  +AS W    ++      + B+ D+ +
SLR   : 425    HGMVDTVWYRPPVSTLWLLVAIVASQWASAQARLEASKEENEDKPL   471
```

Fig. 3

```
Wild type    GGGCT-AGCCCGGATCGCGGCGGCCTATTGGGCCC   (SEQ ID NO:6)
IL-2 ApaI side    GGGCT-AG--G-GATCGC-GCCTATTGGGCCC   (SEQ ID NO:7)
IL-2 BamHI side   GGGCTCA-----GATCGC-GCCTATTGGGCCC   (SEQ ID NO:8)
IctB              G  L  A  A  I  A  A  Y  W  A  L    (SEQ ID NO:9)
```

Fig. 5

SEQUENCE LISTING (1) GENERAL INFORMATION:

(iii) NUMBER OF SEQUENCES:    9

(2) INFORMATION FOR SEQ ID NO:1:

(i) SEQUENCE CHARACTERISTICS:
        (A) LENGTH:4957
        (B) TYPE:nucleic acid
        (C) STRANDEDNESS:double
        (D) TOPOLOGY:linear (xi) SEQUENCE DESCRIPTION: SEQ ID NO:1:

| | | | | | |
|---|---|---|---|---|---|
| AAGCTTGGAT | TGAAGCGATC | GGGGTCAATC | CCAGCGATGA | TCCTCAGTTC | 50 |
| CTCCTGATGG | TCGATCCCTT | TAGCGCCAAG | ATTGAGGATC | TGCTGCAAGG | 100 |
| GCTGGATTTC | GCCTATCCCG | AGGCCGTGAA | AGTGGGCGGA | TTGGCCAGTG | 150 |
| GTTTGGGGGC | AGAGTCAGCG | ATCGCCAGCT | TGTTTTTTCA | AGACCGACAG | 200 |
| GTCGATGGCG | TGATTGGGCT | AGCCCTCAGT | GGCAATGTCC | AGCTGCAGGC | 250 |
| GATCGTGGCT | CAGGGCTGTC | GTCCAGTTGG | CCCGCTTTGG | CATGTGGCAG | 300 |
| CGGCGGAGCG | CAACATTCTG | CGGCAACTTC | AGACCGAAGA | CGAGGAACCG | 350 |
| ATCGCCGCGC | TGCAAGCCCT | ACAGTCAGTC | CTGCGTGATC | TCTCCCCTGA | 400 |
| ATTACAGCGA | TCGCTCTGTG | TGGGCCTGGC | CTGCAATTCT | TTCCAAACGG | 450 |
| TATTACAACC | GGGCGACTTC | CTGATCCGTA | ACCTGCTGGG | GTTTGATCCC | 500 |
| CGCACTGGTG | CTGTAGCAAT | CGGCGATCGC | ATTCGAGTTG | GGCAGCGGCT | 550 |
| GCAGCTGCAC | GTACGGGATG | CCCAGACAGC | GGCGGATGAC | CTCGAGCGGC | 600 |
| AACTGGGCA | ATGGTGCCGG | CAGCATGCGA | CAAAACCAGC | AGCTTCCCTC | 650 |
| TTGTTTTCCT | GCTTGGGGCG | CGGCAAGCCC | TTCTATCAGC | AGGCCAACTT | 700 |
| CGAGTCGCAA | CTGATTCAGC | ATTACCTCTC | AGAGCTGCCC | CTAGCTGGCT | 750 |
| TTTTCTGTAA | TGGCGAAATC | GGCCCGATCG | CTGGCAGCAC | CTACCTGCAT | 800 |
| GGCTACACAT | CGGTGCTGGC | TTTGCTGTCG | GCCAAAACTC | ACTAGCGCCA | 850 |
| GCGAGACCTG | ATTGTCGATC | TGCTGAGCGC | GACTGTAGCG | CTGGAAATAG | 900 |
| GCCCGGACCT | GAGCAGGCGC | ATCGGCCAAG | CTGACCGTAG | TATCACCGTC | 950 |
| AGCCACCCCC | GCCCAGAAAT | TCCGCAACAT | CGGCAGGAGA | GCGATCGCCT | 1000 |
| CCGCCTCCGA | TAAATTCAAC | GGCTCATGGG | TCAACAGGCG | GATCAAGTAC | 1050 |
| TCTGACTGCG | ATCGCCATCC | ATTCCCGCCG | AAAACGTTTG | TAAATCAGTC | 1100 |
| TTGATCCGGT | AGCGATCGCA | CCCGACGGGA | CTCTAGTTCT | AGTTGCCAAC | 1150 |
| CTTCAGCGGC | AGGTTGTACG | GTTCCGAGTC | GGTAGGGATG | GGGATAGCTG | 1200 |
| ACCAAGGAAC | CGGTCGTGAC | TTCCCAGAGA | GCACCTTGCT | GACTGGTGGC | 1250 |
| TTGGATGTGG | AGGTGGCCTG | TGAAGATCAC | CGAGACGCTG | CCCGCTTCGA | 1300 |

-continued

| | |
|---|---|
| GGATTGATCG CAATTCCTCG GCATTTTCTA AGATGTAGCG CTGACCAAGC | 1350 |
| GGATGCTGCT GTTGATCGGG CAGATGCTCC AACACATTGT GGTGAATCAT | 1400 |
| CACCCAGCGT TGGCTAGCGG TGGAAGTGGC GAGTTCTTGT TGCAGCCAGT | 1450 |
| TGAGTTGCGC GCAATCGACT CGCCCCCGAT GCAGTTGATG GCCCGCTTCA | 1500 |
| TCAAAAGCGA TCGAATTCAG CGCAAACAGA TCGAGATCCG GTGCGATCGT | 1550 |
| GCAGCGATAG TAGGGGCGAT CGCTCGTGAA GCCAAAGTCT TGATAGAGCT | 1600 |
| CGACAAACTC GGCCACACCG GTGCGATCGC GATCGCTCGC TGCGGCGGGC | 1650 |
| ATATCGTGGT TGCCCGGCAC CACATAGACC GGATAGGGCA ACTGGCGCAA | 1700 |
| TTGTTGCAGC AGCCACTGAT GGTTTTCCCG CTCCCCGTGC TGGGTTAAAT | 1750 |
| CCCCCGGCAG CAACAGGAAG TCCAAATCCA GCGCTGCCAG TTCTGTCAGG | 1800 |
| ATTTGCTCAA AAGCCGGAAT GCTGCACTCA ATCAAATGGA AGCGATGGGG | 1850 |
| ATGGTGCCAA ATTGTCTGCG GCAGTCCAAT GTGGAGATCG CTCAGCAGCG | 1900 |
| CAAATCGAAA CGCTCGGTTC ATTGCCATCC CCTCAGCTAT CGAGCCCGAT | 1950 |
| TCTAGGCGAA GCTAGGTCGA GTCCGTTGTC TTCAGTTGCA AGCATTCATG | 2000 |
| GCCAGAGTTC GCGTTCGGCA GCACGTCAAT CCGCTCTCTC AGAAATTCCA | 2050 |
| AGTGGTCACG ACTTGGCCGG ATTGGCAACA GGTCTATGCG GACTGCGATC | 2100 |
| GCCCGCTGCA TTTGGATATT GGCTGTGCTC GCGGGCGCTT TCTGCTGGCA | 2150 |
| ATGGCGACAC GACAACCTGA GTGGAATTAT CTGGGCTGG AAAATTCGTGA | 2200 |
| GCCGCTGGTA GATGAGGCGA ACGCGATCGC CCGCGAACGT GAACTGACCA | 2250 |
| ATCTCTACTA CCACTTCAGC AACGCCAATT TGGACTTGGA ACCGCTGCTG | 2300 |
| CGATCGCTGC CGACAGGGAT TTTGCAGCGG GTCAGCATTC AGTTCCCGGA | 2350 |
| TCCTTGGTTC AAGAAACGCC ATCAAAAGCG ACGCGTCGTC CAGCCGGAAC | 2400 |
| TGGTGCAAGC CCTCGCGACT GCGTTACCTG CTGGTGCAGA GGTCTTTCTG | 2450 |
| CAATCCGATG TGCTGGAAGT GCAGGCAGAG ATGTGCGAAC ACTTTGCGGC | 2500 |
| GGAACCCCGC TTTCAGCGCA CCTGCTTGGA CTGGCTGCCG AAAATCCGC | 2550 |
| TGCCCGTCCC GACCGAGCGC GAAATTGCCG TTCAAAACAA ACAGTTGCCA | 2600 |
| GTCTACCGTG CTCTCTTCAT TCGGCAGCCA GCGGACTAAG CTCTTAAGGC | 2650 |
| AAGCGTTGAC GCGATCGCGA TGACTGTCTG GCAAACTCTG ACTTTTGCCC | 2700 |
| ATTACCAACC CCAACAGTGG GGCCACAGCA GTTTCTTGCA TCGGCTGTTT | 2750 |
| GGCAGCCTGC GAGCTTGGCG GGCCTCCAGC CAGCTGTTGG TTTGGTCTGA | 2800 |
| GGCACTGGGT GGCTTCTTGC TTGCTGTCGT CTACGGTTCG GCTCCGTTTG | 2850 |
| TGCCCAGTTC CGCCCTAGGG TTGGGGCTAG CCGCGATCGC GGCCTATTGG | 2900 |
| GCCCTGCTCT CGCTGACAGA TATCGATCTG CGGCAAGCAA CCCCCATTCA | 2950 |
| CTGGCTGGTG CTGCTCTACT GGGGCGTCGA TGCCCTAGCA ACGGGACTCT | 3000 |
| CACCCGTACG CGCTGCAGCT TTAGTTGGGC TAGCCAAACT GACGCTCTAC | 3050 |
| CTGTTGGTTT TTGCCCTAGC GGCTCGGGTT CTCCGCAATC CCCGTCTGCG | 3100 |
| ATCGCTGCTG TTCTCGGTCG TCGTGATCAC ATCGCTTTTT GTCAGTGTCT | 3150 |
| ACGGCCTCAA CCAATGGATC TACGGCGTTG AAGAGCTGGC GACTTGGGTG | 3200 |
| GATCGCAACT CGGTTGCCGA CTTCACCTCA CGGGTTTACA GCTATCTGGG | 3250 |
| CAACCCCAAC CTGCTGGCTG CTTATCTGGT GCCGACGACT GCCTTTTCTG | 3300 |

| | |
|---|---|
| CAGCAGCGAT CGGGGTGTGG CGCGGCTGGC TCCCCAAGCT GCTGGCGATC | 3350 |
| GCTGCGACAG GTGCGAGCAG CTTATGTCTG ATCCTCACCT ACAGTCGCGG | 3400 |
| TGGCTGGCTG GGTTTTGTCG CCATGATTTT TGTCTGGGCG TTATTAGGGC | 3450 |
| TCTACTGGTT TCAACCCCGT CTACCCGCAC CCTGGCGACG CTGGCTATTC | 3500 |
| CCAGTCGTAT TGGGTGGACT AGTCGCGGTG CTCTTGGTGG CGGTGCTTGG | 3550 |
| ACTTGAGCCG TTGCGCGTGC GCGTGTTGAG CATCTTTGTG GGGCGTGAAG | 3600 |
| ACAGCAGCAA CAACTTCCGG ATCAATGTCT GGCTGGCGGT GCTGCAGATG | 3650 |
| ATTCAAGATC GGCCTTGGCT GGGCATCGGC CCCGGCAATA CCGCCTTTAA | 3700 |
| CCTGGTTTAT CCCCTCTATC AACAGGCGCG CTTTACGGCG TTGAGCGCCT | 3750 |
| ACTCCGTCCC GCTGGAAGTC GCGGTTGAGG GCGGACTACT GGGCTTGACG | 3800 |
| GCCTTCGCTT GGCTGCTGCT GGTCACGGCG GTGACGGCGG TGCGGCAGGT | 3850 |
| GAGCCGACTG CGGCGCGATC GCAATCCCCA AGCCTTTTGG TTGATGGCTA | 3900 |
| GCTTGGCCGG TTTGGCAGGA ATGCTGGGTC ACGGTCTGTT TGATACCGTG | 3950 |
| CTCTATCGAC CGGAAGCCAG TACGCTCTGG TGGCTCTGTA TTGGAGCGAT | 4000 |
| CGCGAGTTTC TGGCAGCCCC AACCTTCCAA GCAACTCCCT CCAGAAGCCG | 4050 |
| AGCATTCAGA CGAAAAAATG TAGCGGGCTC CCCAACAAAT TCCTGTGCAC | 4100 |
| CCGACTGGAT CCACCACCTA AACTGGATCC CAAAGGTATC CGGTGGATCT | 4150 |
| AGGGTCATAA CGAACTCCGA CCGCGATCGC GTCCGCGAAC TGAACCTCCA | 4200 |
| TCGCACCGAA GCGGAGTTCG TTAGTCGTTG AAGAGCCAAT GCTAGAGGGG | 4250 |
| GCTGCCGAAG CAGTTGGGCT GGAAGCAGGC TGCGAGAAGC CACCCGCATC | 4300 |
| CAAGGCAAAG TTCAGCCGAC CTTCCGCAAA GACTACGATC GCCACGGCGG | 4350 |
| CTCTGCCAGC TAAGTCAGCG CTGGGTTAGT TGTCATAGCA GTCCGCAGAC | 4400 |
| AAGTTAGGAC AACTTCATAG AGGGACTCGC TCAGAGTCAA CAGCCGCTGT | 4450 |
| CCGTGGGGGT GCGCAATCAC CCCCACACCC ACGCACTGGG GGACTCGACT | 4500 |
| CCCCCAGGCC CCCCGCAACA AGATTTCGGA TAAGGGGCAT CGGCTGAATC | 4550 |
| GCGATCGCTG CGGGTAAAAC TAGCCGGTGT TAGCCATGGG TTTGAGACTA | 4600 |
| ATCGGCACGG GGCAAAACGT CCTGATTTAT TTGCTCAATG TGATAGGTTA | 4650 |
| CATCGTCAAA AACAAGGCCC AAGAGGTAGG AAAAATCACG ACCGCCCAAG | 4700 |
| TCCGAGGGCT TTGCTGTTGG GAGCGACCTA GGGCAGACTA GACAGAGCAT | 4750 |
| TGCTGTGAGC CAAAGCGCCT TCAATTGCTG GCGGCTGTGG GTTTTTCGGA | 4800 |
| GGTTGCCAAA TGAAAGACCT TTTCGTCAAT GTCCTCCGCT ATCCCCGCTA | 4850 |
| CTTCATCACC TTCCAGCTGG GTATTTTTTA GTCGATCTAC CAGTGGGTGC | 4900 |
| GGCCGATGGT TCGCAACCCA GTCGCGGCTT GGGCGCTGCT AGGCTTTGGA | 4950 |
| GTTTCGA | 4957 |

(2) INFORMATION FOR SEQ ID NO:2:

(i) SEQUENCE CHARACTERISTICS:
        (A) LENGTH:1404
        (B) TYPE:nucleic acid
        (C) STRANDEDNESS:double
        (D) TOPOLOGY:linear (xi) SEQUENCE DESCRIPTION: SEQ ID NO:2:

```
ATGACTGTCT GGCAAACTCT GACTTTTGCC CATTACCAAC CCCAACAGTG        50

GGGCCACAGC AGTTTCTTGC ATCGGCTGTT TGGCAGCCTG CGAGCTTGGC       100

GGGCCTCCAG CCAGCTGTTG GTTTGGTCTG AGGCACTGGG TGGCTTCTTG       150

CTTGCTGTCG TCTACGGTTC GGCTCCGTTT GTGCCCAGTT CCGCCCTAGG       200

GTTGGGGCTA GCCGCGATCG CGGCCTATTG GGCCCTGCTC TCGCTGACAG       250

ATATCGATCT GCGGCAAGCA ACCCCCATTC ACTGGCTGGT GCTGCTCTAC       300

TGGGGCGTCG ATGCCCTAGC AACGGGACTC TCACCCGTAC GCGCTGCAGC       350

TTTAGTTGGG CTAGCCAAAC TGACGCTCTA CCTGTTGGTT TTTGCCCTAG       400

CGGCTCGGGT TCTCCGCAAT CCCCGTCTGC GATCGCTGCT GTTCTCGGTC       450

GTCGTGATCA CATCGCTTTT TGTCAGTGTC TACGGCCTCA ACCAATGGAT       500

CTACGGCGTT GAAGAGCTGG CGACTTGGGT GGATCGCAAC TCGGTTGCCG       550

ACTTCACCTC ACGGGTTTAC AGCTATCTGG CAACCCCAA CCTGCTGGCT        600

GCTTATCTGG TGCCGACGAC TGCCTTTTCT GCAGCAGCGA TCGGGGTGTG       650

GCGCGGCTGG CTCCCCAAGC TGCTGGCGAT CGCTGCGACA GGTGCGAGCA       700

GCTTATGTCT GATCCTCACC TACAGTCGCG GTGGCTGGCG GGGTTTTGTC       750

GCCATGATTT TTGTCTGGGC GTTATTAGGG CTCTACTGGT TTCAACCCCG       800

TCTACCCGCA CCCTGGCGAC GCTGGCTATT CCCAGTCGTA TTGGGTGGAC       850

TAGTCGCGGT GCTCTTGGTG GCGGTGCTTG GACTTGAGCC GTTGCGCGTG       900

CGCGTGTTGA GCATCTTTGT GGGGCGTGAA GACAGCAGCA ACAACTTCCG       950

GATCAATGTC TGGCTGGCGG TGCTGCAGAT GATTCAAGAT CGGCCTTGGC      1000

TGGGCATCGG CCCCGGCAAT ACCGCCTTTA ACCTGGTTTA TCCCCTCTAT      1050

CAACAGGCGC GCTTTACGGC GTTGAGCGCC TACTCCGTCC CGCTGGAAGT      1100

CGCGGTTGAG GGCGGACTAC TGGGCTTGAC GGCCTTCGCT TGGCTGCTGC      1150

TGGTCACGGC GGTGACGGCG GTGCGGCAGG TGAGCCGACT GCGGCGCGAT      1200

CGCAATCCCC AAGCCTTTTG GTTGATGGCT AGCTTGGCCG GTTTGGCAGG      1250

AATGCTGGGT CACGGTCTGT TTGATACCGT GCTCTATCGA CCGGAAGCCA      1300

GTACGCTCTG GTGGCTCTGT ATTGGAGCGA TCGCGAGTTT CTGGCAGCCC      1350

CAACCTTCCA AGCAACTCCC TCCAGAAGCC GAGCATTCAG ACGAAAAAAT      1400

GTAG                                                        1404
```

(2) INFORMATION FOR SEQ ID NO:3:

(i) SEQUENCE CHARACTERISTICS:
        (A) LENGTH:467
        (B) TYPE:amino acid
        (C) STRANDEDNESS:single
        (D) TOPOLOGY:linear (xi) SEQUENCE DESCRIPTION: SEQ ID NO:3:

```
Met Thr Val Trp Gln Thr Leu Thr Phe Ala His Tyr Gln Pro Gln
              5                  10                  15

Gln Trp Gly His Ser Ser Phe Leu His Arg Leu Phe Gly Ser Leu
             20                  25                  30

Arg Ala Trp Arg Ala Ser Ser Gln Leu Leu Val Trp Ser Glu Ala
             35                  40                  45
```

-continued

```
Leu Gly Gly Phe Leu Leu Ala Val Val Tyr Gly Ser Ala Pro Phe
                50                  55                  60

Val Pro Ser Ser Ala Leu Gly Leu Gly Leu Ala Ala Ile Ala Ala
                65                  70                  75

Tyr Trp Ala Leu Leu Ser Leu Thr Asp Ile Asp Leu Arg Gln Ala
                80                  85                  90

Thr Pro Ile His Trp Leu Val Leu Leu Tyr Trp Gly Val Asp Ala
                95                 100                 105

Leu Ala Thr Gly Leu Ser Pro Val Arg Ala Ala Ala Leu Val Gly
               110                 115                 120

Leu Ala Lys Leu Thr Leu Tyr Leu Leu Val Phe Ala Leu Ala Ala
               125                 130                 135

Arg Val Leu Arg Asn Pro Arg Leu Arg Ser Leu Leu Phe Ser Val
               140                 145                 150

Val Val Ile Thr Ser Leu Phe Val Ser Val Tyr Gly Leu Asn Gln
               155                 160                 165

Trp Ile Tyr Gly Val Glu Glu Leu Ala Thr Trp Val Asp Arg Asn
               170                 175                 180

Ser Val Ala Asp Phe Thr Ser Arg Val Tyr Ser Tyr Leu Gly Asn
               185                 190                 195

Pro Asn Leu Leu Ala Ala Tyr Leu Val Pro Thr Thr Ala Phe Ser
               200                 205                 210

Ala Ala Ala Ile Gly Val Trp Arg Gly Trp Leu Pro Lys Leu Leu
               215                 220                 225

Ala Ile Ala Ala Thr Gly Ala Ser Ser Leu Cys Leu Ile Leu Thr
               230                 235                 240

Tyr Ser Arg Gly Gly Trp Leu Gly Phe Val Ala Met Ile Phe Val
               245                 250                 255

Trp Ala Leu Leu Gly Leu Tyr Trp Phe Gln Pro Arg Leu Pro Ala
               260                 265                 270

Pro Trp Arg Arg Trp Leu Phe Pro Val Val Leu Gly Gly Leu Val
               275                 280                 285

Ala Val Leu Leu Val Ala Val Leu Gly Leu Glu Pro Leu Arg Val
               290                 295                 300

Arg Val Leu Ser Ile Phe Val Gly Arg Glu Asp Ser Ser Asn Asn
               305                 310                 315

Phe Arg Ile Asn Val Trp Leu Ala Val Leu Gln Met Ile Gln Asp
               320                 325                 330

Arg Pro Trp Leu Gly Ile Gly Pro Gly Asn Thr Ala Phe Asn Leu
               335                 340                 345

Val Tyr Pro Leu Tyr Gln Gln Ala Arg Phe Thr Ala Leu Ser Ala
               350                 355                 360

Tyr Ser Val Pro Leu Glu Val Ala Val Glu Gly Gly Leu Leu Gly
               365                 370                 375

Leu Thr Ala Phe Ala Trp Leu Leu Val Thr Ala Val Thr Ala
               380                 385                 390

Val Arg Gln Val Ser Arg Leu Arg Arg Asp Arg Asn Pro Gln Ala
               395                 400                 405

Phe Trp Leu Met Ala Ser Leu Ala Gly Leu Ala Gly Met Leu Gly
               410                 415                 420

His Gly Leu Phe Asp Thr Val Leu Tyr Arg Pro Glu Ala Ser Thr
               425                 430                 435

Leu Trp Trp Leu Cys Ile Gly Ala Ile Ala Ser Phe Trp Gln Pro
```

440              445              450
Gln Pro Ser Lys Gln Leu Pro Pro Glu Ala Glu His Ser Asp Glu
                455              460              465
Lys Met (2) INFORMATION FOR SEQ ID NO:4:

(i) SEQUENCE CHARACTERISTICS:
        (A) LENGTH:1425
        (B) TYPE:nucleic acid
        (C) STRANDEDNESS:double
        (D) TOPOLOGY:linear (xi) SEQUENCE DESCRIPTION: SEQ ID NO:4:

| | |
|---|---:|
| ATGGTGTCTC CCATCTCTAT CTGGCGATCG CTGATGTTTG GCGGTTTTTC | 50 |
| CCCCCAGGAA TGGGGCCGGG GCAGTGTGCT CCATCGTTTG GTGGGCTGGG | 100 |
| GACAGAGTTG GATACAGGCT AGTGTGCTCT GGCCCCACTT CGAGGCATTG | 150 |
| GGTACGGCTC TAGTGGCAAT AATTTTTATT GCGGCTCCCT TCACCTCCAC | 200 |
| CACCATGTTG GCATTTTTA TGCTGCTCTG TGGAGCCTTT TGGGCTCTGC | 250 |
| TGACCTTTGC TGATCAACCA GGGAAGGGTT TGACTCCCAT CCATGTTTTA | 300 |
| GTTTTTGCCT ACTGGTGCAT TTCGGCGATC GCCGTGGGAT TTTCTCCGGT | 350 |
| AAAAATGGCG GCGGCGTCGG GGTTAGCGAA ATTAACAGCT AATTTATGTC | 400 |
| TGTTTCTACT GGCGGCGAGG TTATTGCAAA ACAAACAATG GTTGAACCGG | 450 |
| TTAGTAACCG TTGTTTTACT GGTAGGGCTA TTGGTGGGGA GTTACGGTCT | 500 |
| GCGACAACAG GTGGACGGGG TAGAACAGTT AGCCACTTGG AATGACCCCA | 550 |
| CCTCTACCTT GGCCCAGGCC ACTAGGGTAT ATAGCTTTTT AGGTAATCCC | 600 |
| AATCTCTTGG CGGCTTACCT GGTGCCCATG ACGGGTTTGA GCTTGAGTGC | 650 |
| CCTGGTGGTA TGGCGACGGT GGTGGCCCAA ACTGCTGGGA GCAACCATGG | 700 |
| TGATTGTTAA CCTACTCTGT CTCTTTTTTA CCCAGAGCCG GGGCGGTTGG | 750 |
| CTAGCAGTGC TGGCCCTGGG AGCTACCTTC CTGGCCCTTT GTTACTTCTG | 800 |
| GTGGTTACCC CAATTACCCA AATTTTGGCA ACGGTGGTCT TTGCCCCTGG | 850 |
| CGATCGCCGT GGCGGTTATA TTAGGTGGGG GAGCGTTGAT TGCGGTGGAA | 900 |
| CCGATTCGAC TCAGGGCCAT GAGCATTTTT GCTGGGCGGG AAGACAGCAG | 950 |
| TAATAATTTC CGCATCAATG TTTGGGAAGG GGTAAAAGCC ATGATCCGAG | 1000 |
| CCCGCCCTAT CATTGGCATT GGCCCAGGTA ACGAAGCCTT TAACCAAATT | 1050 |
| TATCCTTACT ATATGCGGCC CCGCTTCACC GCCCTGAGTG CCTATTCCAT | 1100 |
| TTACCTAGAA ATTTTGGTGG AAACGGGTGT AGTTGGTTTT ACCTGTATGC | 1150 |
| TCTGGCTGTT GGCCGTTACC CTAGGCAAAG GCGTAGAACT GGTTAAACGC | 1200 |
| TGTCGCCAAA CCCTCGCCCC GGAAGGCATC TGGATTATGG GGGCTTTAGC | 1250 |
| GGCGATCATC GGTTTGTTGG TCCACGGCAT GGTAGATACA GTCTGGTACC | 1300 |
| GTCCCCCGGT GAGCACTTTG TGGTGGTTGC TAGTGGCCAT TGTTGCTAGT | 1350 |
| CAGTGGGCCA GCGCCCAGGC CCGTTTGGAG GCCAGTAAAG AAGAAAATGA | 1400 |
| GGACAAACCT CTTCTTGCTT CATAA | 1425 |

(2) INFORMATION FOR SEQ ID NO:5:

-continued

```
    (i) SEQUENCE CHARACTERISTICS:
        (A) LENGTH:474
        (B) TYPE:amino acid
        (C) STRANDEDNESS:single
        (D) TOPOLOGY:linear (xi) SEQUENCE DESCRIPTION: SEQ ID NO:5:

Met Val Ser Pro Ile Ser Ile Trp Arg Ser Leu Met Phe Gly Gly
                 5                  10                  15

Phe Ser Pro Gln Glu Trp Gly Arg Gly Ser Val Leu His Arg Leu
                 20                  25                  30

Val Gly Trp Gly Gln Ser Trp Ile Gln Ala Ser Val Leu Trp Pro
                 35                  40                  45

His Phe Glu Ala Leu Gly Thr Ala Leu Val Ala Ile Ile Phe Ile
                 50                  55                  60

Ala Ala Pro Phe Thr Ser Thr Met Leu Gly Ile Phe Met Leu
                 65                  70                  75

Leu Cys Gly Ala Phe Trp Ala Leu Leu Thr Phe Ala Asp Gln Pro
                 80                  85                  90

Gly Lys Gly Leu Thr Pro Ile His Val Leu Val Phe Ala Tyr Trp
                 95                 100                 105

Cys Ile Ser Ala Ile Ala Val Gly Phe Ser Pro Val Lys Met Ala
                110                 115                 120

Ala Ala Ser Gly Leu Ala Lys Leu Thr Ala Asn Leu Cys Leu Phe
                125                 130                 135

Leu Leu Ala Ala Arg Leu Leu Gln Asn Lys Gln Trp Leu Asn Arg
                140                 145                 150

Leu Val Thr Val Val Leu Leu Val Gly Leu Leu Val Gly Ser Tyr
                155                 160                 165

Gly Leu Arg Gln Gln Val Asp Gly Val Glu Gln Leu Ala Thr Trp
                170                 175                 180

Asn Asp Pro Thr Ser Thr Leu Ala Gln Ala Thr Arg Val Tyr Ser
                185                 190                 195

Phe Leu Gly Asn Pro Asn Leu Leu Ala Ala Tyr Leu Val Pro Met
                200                 205                 210

Thr Gly Leu Ser Leu Ser Ala Leu Val Val Trp Arg Arg Trp Trp
                215                 220                 225

Pro Lys Leu Leu Gly Ala Thr Met Val Ile Val Asn Leu Leu Cys
                230                 235                 240

Leu Phe Phe Thr Gln Ser Arg Gly Gly Trp Leu Ala Val Leu Ala
                245                 250                 255

Leu Gly Ala Thr Phe Leu Ala Leu Cys Tyr Phe Trp Trp Leu Pro
                260                 265                 270

Gln Leu Pro Lys Phe Trp Gln Arg Trp Ser Leu Pro Leu Ala Ile
                275                 280                 285

Ala Val Ala Val Ile Leu Gly Gly Ala Leu Ile Ala Val Glu
                290                 295                 300

Pro Ile Arg Leu Arg Ala Met Ser Ile Phe Ala Gly Arg Glu Asp
                305                 310                 315

Ser Ser Asn Asn Phe Arg Ile Asn Val Trp Glu Gly Val Lys Ala
                320                 325                 330

Met Ile Arg Ala Arg Pro Ile Ile Gly Ile Gly Pro Gly Asn Glu
                335                 340                 345

Ala Phe Asn Gln Ile Tyr Pro Tyr Tyr Met Arg Pro Arg Phe Thr
                350                 355                 360
```

```
Ala Leu Ser Ala Tyr Ser Ile Tyr Leu Glu Ile Leu Val Glu Thr
                365                 370                 375
Gly Val Val Gly Phe Thr Cys Met Leu Trp Leu Leu Ala Val Thr
                380                 385                 390
Leu Gly Lys Gly Val Glu Leu Val Lys Arg Cys Arg Gln Thr Leu
                395                 400                 405
Ala Pro Glu Gly Ile Trp Ile Met Gly Ala Leu Ala Ala Ile Ile
                410                 415                 420
Gly Leu Leu Val His Gly Met Val Asp Thr Val Trp Tyr Arg Pro
                425                 430                 435
Pro Val Ser Thr Leu Trp Trp Leu Leu Val Ala Ile Val Ala Ser
                440                 445                 450
Gln Trp Ala Ser Ala Gln Ala Arg Leu Glu Ala Ser Lys Glu Glu
                455                 460                 465
Asn Glu Asp Lys Pro Leu Leu Ala Ser
                470
```

(2) INFORMATION FOR SEQ ID NO:6:

(i) SEQUENCE CHARACTERISTICS:
        (A) LENGTH:31
        (B) TYPE:nucleic acid
        (C) STRANDEDNESS:double
        (D) TOPOLOGY:linear (xi) SEQUENCE DESCRIPTION: SEQ ID NO:6:

GGGCTAGCCG CGATCGCGGC CTATTGGGCC C            31

(2) INFORMATION FOR SEQ ID NO:7:

(i) SEQUENCE CHARACTERISTICS:
        (A) LENGTH:27
        (B) TYPE:nucleic acid
        (C) STRANDEDNESS:double
        (D) TOPOLOGY:linear (xi) SEQUENCE DESCRIPTION: SEQ ID NO:7:

GGGCTAGGGA TCGCGCCTAT TGGGCCC            27

(2) INFORMATION FOR SEQ ID NO:8:

(i) SEQUENCE CHARACTERISTICS:
        (A) LENGTH:26
        (B) TYPE:nucleic acid
        (C) STRANDEDNESS:double
        (D) TOPOLOGY:linear (xi) SEQUENCE DESCRIPTION: SEQ ID NO:8:

GGGCTCAGAT CGCGCCTATT GGGCCC            26

(2) INFORMATION FOR SEQ ID NO:9:

(i) SEQUENCE CHARACTERISTICS:
        (A) LENGTH:11
        (B) TYPE:amino acid
        (C) STRANDEDNESS:single
        (D) TOPOLOGY:linear (xi) SEQUENCE DESCRIPTION: SEQ ID NO:9:

```
Gly Leu Ala Ala Ile Ala Ala Tyr Trp Ala Leu
                 5                  10
```

ENHANCING INORGANIC CARBON FIXATION BY PHOTOSYNTHETIC ORGANISMS

FIELD AND BACKGROUND OF THE INVENTION

The present invention relates to a method of enhancing inorganic carbon fixation by photosynthetic organisms, nucleic acid molecules for effecting the method, and transformed plants characterized by enhanced inorganic carbon fixation.

Photosynthesis is a process executed by photosynthetic organisms by which, inorganic carbon (Ci), such as $CO_2$ and $HCO_3^-$, is incorporated into organic compounds using the energy of photon radiation. Photosynthetic organisms, such as, soil grown and aquatic plants and cyanobacteria (blue-green algae), depend on the organic compounds produced via photosynthesis for sustenance and growth.

The rate of photosynthesis is determined by several parameters which include but are not limited to, $CO_2$ concentration, $O_2$ concentration, temperature, light intensity, and the water balance in the case of soil grown plants.

Of the above mentioned parameters photosynthesis is largely influenced by the rate with which the carboxylating enzyme ribulose 1,5-bisphosphate carboxylase/oxygenase, (rubisco) can fix available $CO_2$. The rate of $CO_2$ fixation depends on the concentration of $CO_2$ and to a lesser extent on the concentration of $O_2$ which are available to rubisco, since $CO_2$ fixation competes with photorespiration, which is the process of $O_2$ fixation by rubisco. Furthermore, when photosynthesis is rate-limited by the supply of $CO_2$, the imbalance between the light energy input and its dissipation via $CO_2$ fixation, leads to photodynamic damage to the photosynthetic reaction centers (photoinhibition).

Since rubisco possesses a very slow turnover rate, in order to meet the energy requirements of photosynthetic organisms it needs to be present in abundance within the photosynthetic cells thereof (approximately 50% of the soluble protein). The abundance of rubisco leads to deleterious effects to the energetic balance of photosynthetic cells since most available resources of these cells must be allocated to the production of rubisco.

To overcome the problems associated with inefficient $CO_2$ fixation at low $CO_2$ concentrations, many photosynthetic organisms have evolved various mechanisms for concentrating the inorganic carbon exposed to rubisco. Such mechanisms are found in certain higher plants (belonging to the C4 group, including maize and sorghum) and in aquatic photosynthetic organisms. In C4 plants, differential expression and tight regulation of several genes enables cooperation between the mesophyll and bundle sheath cells leading to elevated $CO_2$ concentration in the latter. An initial carboxylation reaction, where $HCO_3^-$ serves as the substrate, occurs in the mesophyll cells. The product is then transferred to the bundle sheath cells where it is decarboxylated (releasing the $CO_2$ fixed in the mesophyll cells) in close proximity to rubisco (confined to these cells). C3 plants, to which most of the crop plants belong, are unable to concentrate $CO_2$ at the site of rubisco and therefore grow poorly (compared to C4 plants) under water-limiting conditions. Due to the large number of genes involved, and to the complexity of their tight, spatial regulation, in the operation of the C4 mechanism, the introduction of the whole C4 $CO_2$ concentrating mechanism to C3 plants is presently impossible.

Many aquatic photosynthetic microorganisms possess inducible mechanisms that concentrate $CO_2$ at the carboxylation site, compensating for the relatively low affinity of rubisco for its substrate, thus allowing acclimation to a wide range of $CO_2$ concentrations [25]. The presence of membrane-located mechanisms for inorganic carbon (Ci) transport are central to these concentrating mechanisms.

Photosynthetic microorganisms including cyanobacteria are also capable of acclimating to a wide range of $CO_2$ concentrations. The process of acclimation is mediated via changes, effected at various cellular levels, which include modulation of gene expression involved in the operation of the $CO_2$ concentrating mechanism (CCM) [1–5]. This mechanism enables these photosynthetic microorganisms to raise the $CO_2$ level at the carboxylation site thus overcoming the large (5 to 20-fold) difference between the $K_m(CO_2)$ of rubisco and the concentration of dissolved $CO_2$ when at equilibrium with the surrounding atmosphere. In cyanobacteria, the components of the CCM include energy-dependent $HCO_3^-$ transport, $CO_2$ conversion to $HCO_3^-$ [3] and highly organized structures, termed carboxysomes, where carbonic anhydrase catalyzes the formation of $CO_2$ from $HCO_3^-$ in close proximity to rubisco [1–3]. The activity of the CCM increases dramatically following transfer from high to low $CO_2$ concentrations mainly due to changes in the Ci transport capabilities and an increase in the number of carboxysomes [3, 6, 7]. Some of the genes involved in the operation of the CCM were identified with the aid of high-$CO_2$-requiring mutants but there is little information on those directly involved in $HCO_3^-$ uptake [3, 4, 8].

The ability to concentrate $CO_2$ provides distinct advantages to photosynthetic organisms. The photosynthetic rate of such $CO_2$ concentrating organisms is not severely affected by lower $CO_2$ concentrations and as a result, the growth and productivity of such organisms are not severely limited by the environmental concentration of $CO_2$, and by water, in the case of soil grown plants.

Therefore, it is highly desirable to enhance $CO_2$ fixation in non $CO_2$ concentrating photosynthetic organisms, such as C3 plants, since in all probability, such an enhancement would directly result in improved growth and productivity.

There are two possible biotechnological approaches with which an enhanced rate of $CO_2$ fixation can be achieved.

One such approach involves the manipulation of rubisco by site directed mutagenesis in order to raise both its affinity and specificity to $CO_2$ (compared with $O_2$) and to further enhance its turnover rate. Although numerous studies were conducted in order to isolate a rubisco mutant which possesses the above mentioned improvements at present no such rubisco mutants have been isolated.

Another approach for enhancing $CO_2$ fixation involves raising the concentration of $CO_2$ outside the cells of higher plants. In higher plants the concentration of $CO_2$ in the air spaces within the leaves is determined by the diffusional flux of $CO_2$ through the stomata from the surrounding air via the unstirred layer around the leaves. The stomatal conductance for $CO_2$ is largely determined by the water balance of the plants. Modulation of stomatal opening by water availability is exercised by plants in order to combat water stress. Stomatal closure, in order to minimize water loss under conditions of water stress, generates a significant resistance to $CO_2$ diffusion leading to a sharp decline in $CO_2$ fixation. Although raising the concentration of $CO_2$ in a closed environment, such as a greenhouse, is commonly practiced in order to raise the diffusional flux of $CO_2$ and as such, raise plant productivity, such a practice however, is not applicable to outdoor grown plants.

Increasing stomatal conductance can theoretically serve to raise plant productivity, but at present, viable mechanisms for enhancing the stomatal $CO_2$ conductivity have not been proposed.

Thus, at present, both of the above mentioned approaches are theoretical and as such cannot be applied to render photosynthetic organisms, such as C3 plants, more efficient at fixing $CO_2$.

There is thus a widely recognized need for, and it would be highly advantageous to have, a method of enhancing the $CO_2$ fixation in photosynthetic organisms, such as higher plants, especially C3 plants.

SUMMARY OF THE INVENTION

According to one aspect of the present invention there is provided a method of enhancing inorganic carbon fixation by a photosynthetic organism, the method comprising the step of transforming cells of the photosynthetic organism with an expressible polynucleotide encoding a polypeptide having a bicarbonate transporter activity. Preferably, the polynucleotide further includes a plant promoter.

According to another aspect of the present invention there is provided a nucleic acid molecule for enhancing inorganic carbon fixation by a photosynthetic organism, the nucleic acid molecule comprising a polynucleotide encoding a polypeptide having a bicarbonate transporter activity. Preferably, the nucleic acid molecule further comprising a plant promoter being upstream to the polynucleotide effective in expressing the polypeptide.

According to yet another aspect of the present invention there is provided a transformed photosynthetic organism comprising the nucleic acid molecule described herein.

According to further features in preferred embodiments of the invention described below, the step of transforming the cells of the photosynthetic organism with the expressible polynucleotide encoding the bicarbonate transporter is effected by a method selected from the group consisting of genetic transformation and transient transformation.

According to still further features in the described preferred embodiments the genetic transformation is effected by a method selected from the group consisting of Agrobaterium mediated transformation, electroporation and particle bombardment.

According to still further features in the described preferred embodiments the transient transformation is effected by a method selected from the group consisting of viral transformation, electroporation and particle bombardment.

According to still further features in the described preferred embodiments the polynucleotide includes (i) a nucleic acid sequence corresponding to at least a portion derived from SEQ ID NO:2, the portion encodes the protein having the bicarbonate transporter activity; (ii) a nucleic acid sequence at least 60% identical to the portion, as determined using the Blast software where gap penalty equals 10 for existence and 10 for extension, average match equals 10 and average mismatch equals −5; (iii) a nucleic acid segment hybridizable with the portion under hybridization conditions of hybridization solution containing 10% dextrane sulfate, 1 M NaCl, 1% SDS and $5 \times 10^6$ cpm $^{32}$p labeled probe, at 65° C., with a final wash solution of 0.2×SSC and 0.1% SDS and final wash at 65° C.; (iv) a man induced variation of the portion; or (v) a naturally occurring variation of the portion.

According to still further features in the described preferred embodiments the polypeptide is at least 70% homologous to SEQ ID NO:3 or a portion thereof having the bicarbonate transporter activity as determined using the Blast software where gap open penalty equals 11, gap extension penalty equals 1 and matrix is blosum62.

According to still further features in the described preferred embodiments the photosynthetic organism is a plant.

According to still further features in the described preferred embodiments the plant is a C3 plant.

According to still further features in the described preferred embodiments the C3 plant is selected from the group consisting of tobacco, tomato, soybeans, potato, cucumber, cotton, wheat, rice and barley.

According to still further features in the described preferred embodiments the plant is a C4 plant.

According to still further features in the described preferred embodiments the C4 plant is selected from the group consisting of corn, sugar cane and sorghum.

According to still further features in the described preferred embodiments the organism is characterized by a photosynthetic rate at least 10% higher as compared to a control non-transformed organism under otherwise identical conditions.

According to still further features in the described preferred embodiments the plant promoter is selected from the group consisting of a constitutive plant promoter, a tissue specific plant promoter and an inducible plant promoter.

According to still further features in the described preferred embodiments (i) the constitutive plant promoter is independently selected from the group consisting of CaMV35S plant promoter, CaMV19S plant promoter, FMV34S plant promoter, sugarcane bacilliform badnavirus plant promoter, CsVMV plant promoter, Arabidopsis ACT2/ACT8 actin plant promoter, Arabidopsis ubiquitin UBQ1 plant promoter, barley leaf thionin BTH6 plant promoter, and rice actin plant promoter; (ii) the tissue specific plant promoter is independently selected from the group consisting of bean phaseolin storage protein plant promoter, DLEC plant promoter, PHSβ plant promoter, zein storage protein plant promoter, conglutin gamma plant promoter from soybean, AT2S1 gene plant promoter, ACT11 actin plant promoter from Arabidopsis, napA plant promoter from Brassica napus and potato patatin gene plant promoter; and (iii) the inducible plant promoter is independently selected from the group consisting of a light-inducible plant promoter derived from the pea rbcS gene, a plant promoter from the alfalfa rbcS gene, DRE, MYC and MYB plant promoters which are active in drought; INT, INPS, prxEa, Ha hsp17.7G4 and RD21 plant promoters active in high salinity and osmotic stress, and hsr203J and str246C plant promoters active in pathogenic stress.

According to still further features in the described preferred embodiments the polynucleotide further includes a sequence element selected from the group consisting of a nucleic acid sequence encoding a transit peptide, an origin of replication for propagation in bacterial cells, at least one sequence element for integration into a plant's genome, a polyadenylation recognition sequence, a transcription termination signal, a sequence encoding a translation start site, a sequence encoding a translation stop site, plant RNA virus derived sequences, plant DNA virus derived sequences, tumor inducing (Ti) plasmid derived sequences and a transposable element derived sequence.

The present invention provides new horizons with respect to crop yields, especially of C3 plants grown under low $CO_2$ and/or under limited water availability, because it accelerates the transport of bicarbonate into plant cells and eventually the chloroplasts to thereby improve the photosynthetic process and as a result carbon fixation.

BRIEF DESCRIPTION OF THE DRAWINGS

The invention is herein described, by way of example only, with reference to the accompanying drawings, wherein:

FIG. 2 shows nucleic acid sequence alignment between ORF467 (ICTB, SEQ ID NO:2) and slr1515 (SLR, SEQ ID NO:4). Vertical lines indicate nucleotide identity. Gaps are indicated by hyphens. Alignment was performed using the Blast software where gap penalty equals 10 for existence and 10 for extension, average match equals 10 and average mismatch equals –5. Identical nucleotides equals 56%.

FIG. 3 shows amino acid sequence alignment between the IctB protein (ICTB, SEQ ID NO:3) and the protein encoded by slr1515 (SLR, SEQ ID NO:5). Identical amino acids are marked by their single letter code between the aligned sequences, similar amino acids are indicated by a plus sign. Alignment was performed using the Blast software where gap open penalty equals 11, gap extension penalty equals 1 and matrix is blosum62. Identical amino acids equals 47%, similar amino acids equals 16%, total homology equals 63%.

FIG. 5 presents DNA sequence homology comparison of a region of ictB found in Synechococcus PCC 7942 and in mutant IL-2. This region was duplicated in the mutant due to a single cross-over event. Compared with the wild type, one additional nucleotide and a deletion of six nucleotides were found in the BamHI side, and 4 nucleotides were deleted in the ApaI side (see FIG. 1). These changes resulted in stop codons in IctB after 168 or 80 amino acids in the BamHI and ApaI sides, respectively. The sequence shown by this Figure starts from the 69$^{th}$ amino acid of ictB.

FIG. 6 is a photograph of a RNA gel blot showing expression of ictB RNA in transgenic Arabidopsis plants. RNA was isolated from wild-type (WT) and 3 independent transgenic plants and subjected to RNA gel blot analysis with a probe for ictB. WT plants were found not to contain transcript(s) that hybridized with the ictB probe. The transgenic lines shown in this Figure were used for the $CO_2$ exchange analysis presented in Table 2.

DESCRIPTION OF THE PREFERRED EMBODIMENTS

Figure 1:
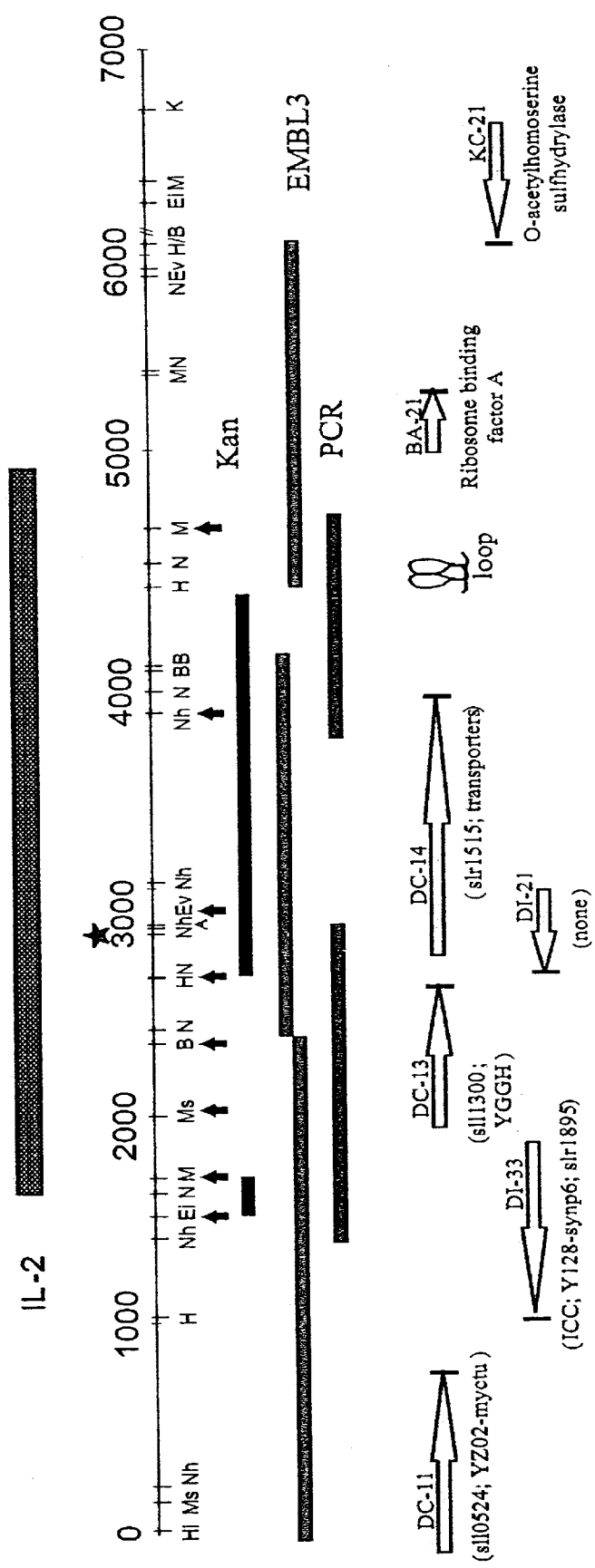
FIG. 1 is a schematic representation of a genomic region in Synechococcus sp. PCC 7942 where an insertion (indicated by a star) of an inactivation library fragment led to the formation of mutant IL-2. DNA sequence is available in the GenBank, Accession number U62616. Restriction sites are marked as: A—ApaI, B—BamHI, Ei—EcoRI, E—EcoRV, H—HincII, Hi—HindIII, K—KpnI, M—MfeI, N—NheI, T—TaqI. Underlined letters represent the terminate position of the DNA fragments that were used as probes. Relevant fragments isolated from an EMBL3 library are marked E1, E2 and E3. P1 and P2 are fragments obtained by PCR. Triangles indicate sites where a cartridge encoding Kan$^r$ was inserted. Open reading frames are marked by an arrow and their similarities to other proteins are noted. Sll and slr (followed by four digits) are the homologous genes in Synechocystis PCC 6803 [23]: YZ02-myctu, Accession No. Q10536; ICC, Accession No. P36650; Y128-SYNP6, Accession No. P05677; YGGH, Accession No. P44648; Ribosome binding factor A homologous to sll0754 and to P45141; O-acetylhomoserine sulfhydrylase homologous to sll0077 and NifS. ORF280 started upstream of the schematic representation presented herein.

The present invention is of a method which can be used to enhance inorganic carbon fixation by photosynthetic organisms. The present invention is further of nucleic acid molecules which can be used to enhance inorganic carbon fixation by photosynthetic organisms. The present invention is further of transformed plants characterized by enhanced inorganic carbon fixation. More specifically, the present invention employs an overexpressed bicarbonate transporter for enhancing carbon fixation in particular C3 plants.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to one aspect of the present invention there is provided a method of enhancing inorganic carbon fixation by a photosynthetic organism.

As used herein in the specification and in the claims section that follows the phrase "photosynthetic organism" includes organisms, both unicellular or multicellular, both prokaryotes or eukaryotes, both soil grown or aquatic, capable of producing complex organic materials, especially carbohydrates, from carbon dioxide using light as the source of energy and with the aid of chlorophyll and optionally associated pigments.

The method according to the present invention is effected by transforming cells of the photosynthetic organism with an expressible polynucleotide encoding a polypeptide having a bicarbonate ($HCO_3^-$) transporter activity.

As used herein in the specification and in the claims section that to follows the term "transform" and its conjugations such as transformation, transforming and transformed, all relate to the process of introducing heterologous nucleic acid sequences into a cell or an organism. The term thus reads on, for example, "genetically modified", "transgenic" and "transfected" or "viral infected" and their conjugations, which may be used herein to further described the present invention. The term relates both to introduction of a heterologous nucleic acid sequence into the genome of an organism and/or into the genome of a nucleic acid containing organelle thereof, such as into a genome of chloroplast or a mitochondrion.

As used herein in the specification and in the claims section that follows the phrase "expressible polynucleotide" refers to a nucleic acid sequence including a promoter sequence and a downstream polypeptide encoding sequence, the promoter sequence is so positioned and constructed so as to direct transcription of the downstream polypeptide encoding sequence.

As used herein in the specification and in the claims section that follows the term "polypeptide" refers also to a protein, in particular a transmembrane protein, which may include a transit peptide, and further to a post translationally modified protein, such as, but not limited to, a phosphorylated protein, glycosylated protein, ubiquitinylated protein, acetylated protein, methylated protein, etc.

As used herein in the specification and in the claims section that follows the phrase "bicarbonate transporter activity" refers to the direct activity of a membrane integrated protein in transporting bicarbonate across a membrane in which it is integrated. Such a membrane can be the cell membrane and/or a membrane of an organelle, such as the chloroplast's outer and inner membrane. Such activity can be effected by direct expenditure of energy, i.e., ATP hydrolysis, which is available both in the cytoplasm and the chloroplast's stroma, or by co- or anti-transport, as effected by co- or antiporters while dissipating a concentration gradient of an ion across a membrane.

According to another aspect of the present invention there is provided a nucleic acid molecule for enhancing inorganic carbon fixation by a photosynthetic organism. The nucleic acid molecule according to this aspect of the present invention includes a polynucleotide encoding a polypeptide having a bicarbonate transporter activity.

As used herein in the specification and in the claims section that follows the term "nucleic acid molecule" includes polynucleotides, constructs and vectors. The terms "construct" and "vector" may be used herein interchangeably.

Such nucleic acid molecule or polynucleotide can be a nucleic acid sequence corresponding to at least a portion derived from SEQ ID NO:2, the portion encodes the protein having the bicarbonate transporter activity.

Alternatively or in addition it can be a nucleic acid sequence at least 60%, preferably at least 65%, more preferably at least 70%, still more preferably at least 75%, yet more preferably at least 80%, more preferably at least 85%, more preferably at least 90%, yet more preferably at least 95%, ideally 95–100% identical to that portion, as determined using the Blast software where gap penalty equals 10 for existence and 10 for extension, average match equals 10 and average mismatch equals −5. It will be appreciated in this respect that SEQ ID NO:2 can be readily used to isolate homologous sequences which can be tested as described in the Examples section that follows for their bicarbonate transport activity. Methods for isolating such homologous sequences are extensively described in, for example, Sambrook et al. [9] and may include hybridization and PCR amplification.

Still alternatively or in addition it can be a nucleic acid segment hybridizable with that portion. Hybridization for long nucleic acids (e.g., above 200 bp in length) is effected according to preferred embodiments of the present invention by stringent or moderate hybridization, wherein stringent hybridization is effected by a hybridization solution containing 10% dextrane sulfate, 1 M NaCl, 1% SDS and $5 \times 10^6$ cpm $^{32}$p labeled probe, at 65° C., with a final wash solution of 0.2×SSC and 0.1% SDS and final wash at 65° C.; whereas moderate hybridization is effected by a hybridization solution containing 10% dextrane sulfate, 1 M NaCl, 1% SDS and $5 \times 10^6$ cpm $^{32}$p labeled probe, at 65° C., with a final wash solution of 1×SSC and 0.1% SDS and final wash at 50° C.

Yet alternatively or in addition it can be a man induced variation, such as site directed or non-specific mutagenesis of that portion. Methods of man induced variation of nucleic acids are well known in the art and are further described in detail in reference [9].

Still alternatively or in addition it can be a naturally occurring variation of that portion. Such variations can be characterized and such sequence alterations isolated by one ordinarily skilled in the art using the assays and procedures described hereinunder in the Examples section that follows.

According to a preferred embodiment of the present invention the polypeptide encoded by the polynucleotide is at least 60%, preferably at least 65%, more preferably at least 70%, still more preferably at least 75%, yet more preferably at least 80%, more preferably at least 85%, more preferably at least 90%, yet more preferably at least 95%, ideally 95–100% homologous (identical+similar) to SEQ ID NO:3 or a portion thereof having the bicarbonate transporter activity as determined using the Blast software where gap open penalty equals 11, gap extension penalty equals 1 and matrix is blosum62.

According to a preferred embodiment of the present invention, the polypeptide includes an N terminal transit peptide fused thereto which serves for directing the polypeptide to a specific membrane. Such a membrane can be, for example, the cell membrane, wherein the polypeptide will serve to transport bicarbonate from the apoplast into the cytoplasm, or, such a membrane can be the outer and preferably the inner chloroplast membrane, wherein the polypeptide will serve to transport bicarbonate from the cytoplasm to the intermembranal space and the stroma, respectively. Transit peptides which function as herein described are well known in the art. Further description of such transit peptides is found in, for example, Johnson et al. The Plant Cell (1990) 2:525–532; Sauer et al. EMBO J. (1990) 9:3045–3050; Mueckler et al. Science (1985) 229:941–945; Von Heijne, Eur. J. Biochem. (1983) 133:17–21; Yon Heijne, J. Mol. Biol. (1986) 189:239–242; Iturriaga et al. The Plant Cell (1989) 1:381–390; McKnight et al., Nucl. Acid Res. (1990) 18:4939–4943; Matsuoka and Nakamura, Proc. Natl. Acad. Sci. USA (1991) 88:834–838. A recent text book entitled "Recombinant proteins from plants", Eds. C. Cunningham and A. J. R. Porter, 1998 Humana Press Totowa, N.J. describe methods for the production of recombinant proteins in plants and methods for targeting the proteins to different compartments in the plant cell. The book by Cunningham and Porter is incorporated herein by reference. It will however be appreciated by one of skills in the art that a large number of membrane integrated proteins fail to possess a removable transit peptide. It is accepted that in such cases a certain amino acid sequence in said proteins serves not only as a structural portion of the protein, but also as a transit peptide.

According to a preferred embodiment, the nucleic acid molecule further includes a plant promoter located upstream to the polynucleotide and being effective in expressing the polypeptide.

As used herein in the specification and in the claims section that follows the phrase "plant promoter" includes a promoter which can direct gene expression in plant cells (including DNA containing organelles). Such a promoter can be derived from a plant, bacterial, viral, fungal or animal origin. Such a promoter can be constitutive, i.e., capable of directing high level of gene expression in a plurality of plant tissues, tissue specific, i.e., capable of directing gene expression in a particular plant tissue or tissues, inducible, i.e., capable of directing gene expression under a stimulus, or chimeric.

Thus, the plant promoter employed can be a constitutive promoter, a tissue specific promoter, an inducible promoter or a chimeric promoter.

Examples of constitutive plant promoters include, without being limited to, CaMV35S and CaMV19S promoters, FMV34S promoter, sugarcane bacilliform badnavirus promoter, CsVMV promoter, Arabidopsis ACT2/ACT8 actin promoter, Arabidopsis ubiquitin UBQ1 promoter, barley leaf thionin BTH6 promoter, and rice actin promoter.

Examples of tissue specific promoters include, without being limited to, bean phaseolin storage protein promoter, DLEC promoter, PHSβ promoter, zein storage protein promoter, conglutin gamma promoter from soybean, AT2S1 gene promoter, ACT11 actin promoter from Arabidopsis, napA promoter from *Brassica napus* and potato patatin gene promoter.

The inducible promoter is a promoter induced by a specific stimuli such as stress conditions comprising, for example, light, temperature, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr203J and str246C active in pathogenic stress.

There are various methods of introducing foreign genes into both monocotyledonous and dicotyledenous plants (Potrykus, I., Annu. Rev. Plant. Physiol., Plant. Mol. Biol. (1991) 42:205–225; Shimamoto et al., Nature (1989) 338:274–276). The principle methods of causing stable integration of exogenous DNA into plant genomic DNA include two main approaches:

(i) Agrobacterium-mediated gene transfer: Klee et al. (1987) Annu. Rev. Plant Physiol. 38:467–486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2–25; Gatenby, in Plant Biotechnology, eds. Kung, S. and Arntzen, C. J., Butterworth Publishers, Boston, Mass. (1989) p. 93–112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52–68; including methods for direct uptake of DNA into protoplasts, Toriyama, K. et al. (1988) Bio/Technology 6:1072–1074. DNA uptake induced by brief electric shock of plant cells: Zhang et al. Plant Cell Rep. (1988) 7:379–384. Fromm et al. Nature (1986) 319:791–793. DNA injection into plant cells or tissues by particle bombardment, Klein et al. Bio/Technology (1988) 6:559–563; McCabe et al. Bio/Technology (1988) 6:923–926; Sanford, Physiol. Plant. (1990) 79:206–209; by the use of micropipette systems: Neuhaus et al., Theor. Appl. Genet. (1987) 75:30–36; Neuhaus and Spangenberg, Physiol. Plant. (1990) 79:213–217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197–209; and Ohta, Proc. Natl. Acad. Sci. USA (1986) 83:715–719.

The Agrobacterium system includes the use of plasmid vectors that contain defined DNA segments that integrate into the plant genomic DNA. Methods of inoculation of the plant tissue vary depending upon the plant species and the Agrobacterium delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1–9. A supplementary approach employs the Agrobacterium delivery system in combination with vacuum infiltration. The Agrobacterium system is especially viable in the creation of transgenic dicotyledenous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

The basic bacterial/plant vector construct will preferably provide a broad host range prokaryote replication origin; a prokaryote selectable marker; and, for Agrobacterium transformations, T DNA sequences for Agrobacterium-mediated transfer to plant chromosomes. Where the heterologous sequence is not readily amenable to detection, the construct will preferably also have a selectable marker gene suitable for determining if a plant cell has been transformed. A general review of suitable markers for the members of the grass family is found in Wilmink and Dons, Plant Mol. Biol. Reptr. (1993) 11:165–185.

Sequences suitable for permitting integration of the heterologous sequence into the plant genome are also recommended. These might include transposon sequences and the like for homologous recombination as well as Ti sequences which permit random insertion of a heterologous expression cassette into a plant genome.

Suitable prokaryote selectable markers include resistance toward antibiotics such as ampicillin or tetracycline. Other DNA sequences encoding additional functions may also be present in the vector, as is known in the art.

The constructs of the subject invention will include an expression cassette for expression of the fusion protein of interest. Usually, there will be only one expression cassette, although two or more are feasible. The recombinant expression cassette will contain in addition to the heterologous sequence one or more of the following sequence elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

Viruses are a unique class of infectious agents whose distinctive features are their simple organization and their mechanism of replication. In fact, a complete viral particle, or virion, may be regarded mainly as a block of genetic material (either DNA or RNA) capable of autonomous replication, surrounded by a protein coat and sometimes by an additional membranous envelope such as in the case of alpha viruses. The coat protects the virus from the environment and serves as a vehicle for transmission from one host cell to another.

Viruses that have been shown to be useful for the transformation of plant hosts include CaV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York pp. 172–189 (1988). Pseudovirus particles for use in expressing foreign DNA in many hosts, including plants, is described in WO 87/06261.

Construction of plant RNA viruses for the introduction and expression of non-viral foreign genes in plants is demonstrated by the above references as well as by Dawson, W. O. et al., Virology (1989) 172:285–292; Takamatsu et al. EMBO J. (1987) 6:307–311; French et al. Science (1986) 231:1294–1297; and Takamatsu et al. FEBS Letters (1990) 269:73–76.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression of non-viral foreign genes in plants is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a fusion protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) in the host to produce the desired fusion protein.

Thus, according to a preferred embodiment of the present invention the polynucleotide or nucleic acid molecule of the present invention further includes one or more sequence elements, such as, but not limited to, a nucleic acid sequence encoding a transit peptide, an origin of replication for propagation in bacterial cells, at least one sequence element for integration into a plant's genome, a polyadenylation recognition sequence, a transcription termination signal, a sequence encoding a translation start site, a sequence encoding a translation stop site, plant RNA virus derived sequences, plant DNA virus derived sequences, tumor inducing (Ti) plasmid derived sequences and a transposable element derived sequence.

According to another preferred embodiment of the present invention, the step of transforming the cells of the photosynthetic organism with the expressible polynucleotide encoding the bicarbonate transporter is effected by a method such as genetic transformation and transient transformation. Genetic transformation can be effected by, for example, Agrobaterium mediated transformation, whereas transient transformation can be effected by, for example, viral transformation. Both transient and genetic transformation can be effected by electroporation, particle bombardment or any of the other methods listed and further described hereinabove.

A technique for introducing heterologous nucleic acid sequences to the genome of the chloroplasts is known. This technique involves the following procedures. First, plant cells are chemically treated so as to reduce the number of chloroplasts per cell to about one. Then, the heterologous nucleic acid is introduced via particle bombardment into the cells with the aim of introducing at least one heterologous nucleic acid molecule into the chloroplasts. The heterologous nucleic acid is selected such that it is integratable into the chloroplast's genome via homologous recombination which is readily effected by enzymes inherent to the chloroplast. To this end, the heterologous nucleic acid includes, in addition to a gene of interest, at least one nucleic acid stretch which is derived from the chloroplast's genome. In addition, the heterologous nucleic acid includes a selectable marker, which serves by sequential selection procedures to ascertain that all or substantially all of the copies of the chloroplast genomes following such selection will include the heterologous nucleic acid. Further details relating to this technique are found in U.S. Pat. Nos. 4,945,050; and 5,693, 507 which are incorporated herein by reference. A polypeptide can thus be produced by the protein expression system of the chloroplast and become integrated into the chloroplast's inner membrane. It will be appreciated that cyanobacterial proteins are expected to express well by the chloroplast expression system.

According to another aspect of the present invention there is provided a transformed photosynthetic organism comprising the nucleic acid molecule or polynucleotide described herein.

According to a preferred embodiment of the present invention the photosynthetic organism is a plant, such as a crop plant. Preferably the plant is a C3 plant, such as, but not limited to, tobacco, tomato, soybeans, potato, cucumber, cotton, wheat, rice and barley because, as further detailed herein, such plants are more sensitive to limited water supply and/or low $CO_2$ atmosphere. However, over expressing C4 plants, such as, but not limited to, corn, sugar cane and sorghum are also expected to enjoy improved $CO_2$ fixation, especially under water-limiting conditions.

According to a preferred embodiment of the present invention the transformed photosynthetic organism is characterized by a photosynthetic rate at least 5%, preferably at least 10%, more preferably at least 15%, yet more preferably at least 25%, still more preferably at least 30%, more preferably at least 40%, more preferably at least 50%, ideally more preferably at least between 50% and 100% higher as compared to a control non-transformed organism under otherwise identical conditions. Such conditions and photosynthesis rate measurement procedures are further described in the Examples section that follows with respect to Table 2.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al. [9]. Other general references are provided throughout this document. The procedures therein are believed to be well known in the art and are provided for the convenience of the reader. All the information contained therein is incorporated herein by reference.

Materials and Experimental Methods

Growth conditions:

Cultures of Synechococcus sp. strain PCC 7942 and mutant IL-2 thereof were grown at 30° C. in $BG_{11}$ medium supplemented with 20 mM Hepes-NaOH pH 7.8 and 25 $\mu$g $mL^{-1}$ kanamycin (in the case of the mutant). The medium was aerated with either 5% v/v $CO_2$ in air (high $CO_2$) or 0.0175% v/v $CO_2$ in air (low $CO_2$) which was prepared by mixing air with $CO_2$-free air at a 1:1 ratio. *Escherichia coli* (strain DH5α) were grown on an LB medium [9] supplemented with either kanamycin (50 $\mu$g/mL) or ampicillin (50 $\mu$g/mL) when required.

Measurements of photosynthesis and Ci uptake:

The rates of inorganic carbon (Ci)-dependent $O_2$ evolution were measured by an $O_2$ electrode as described elsewhere [10] and by a membrane inlet mass spectrometer (MIMS, [6, 11]). The MIMS was also used for assessments of $CO_2$ and $HCO_3^-$ uptake during steady state photosynthesis [6]. Ci fluxes following supply of $CO_2$ or $HCO_3^-$ were determined by the filtering centrifugation technique [10]. High-$CO_2$ grown cells in the log phase of growth were transferred to either low or high $CO_2$ 12 hours before conducting the experiments. Following harvest, the cells were resuspended in 25 mM Hepes-NaOH pH 8.0 and aerated with air (Ci concentration was about 0.4 mM) under light flux of 100 $\mu$mol photon quanta $m^{-2}s^{-1}$ Aliquots were withdrawn, immediately placed in microfuge tubes and kept under similar light and temperature conditions. Small amounts of $^{14}C$—$CO_2$ or $^{14}C$—$HCO_3^-$ which did not affect the final Ci concentration, were injected, and the Ci uptake terminated after 5 seconds by centrifugation.

General DNA manipulations:

Genomic DNA was isolated as described elsewhere [12]. Standard recombinant DNA techniques were used for cloning and Southern analyses [12–13] using the Random Primed DNA Labeling Kit or the DIG system, (Boehringer, Mannheim). Sequence analysis was performed using the Dye Terminator cycle sequencing kit, ABI Prism (377 DNA sequencing Perkin Elmer). The genomic library used here was constructed using Lambda EMBL3/BamHI vector kit (Stratagene, La Jolla, Calif.).

Construction and isolation of mutant IL-2:

A modification of the method developed by Dolganov and Grossman [14] was used to raise and isolate new high-$CO_2$-requiring mutants [4, 5]. Briefly, genomic DNA was digested with TaqI and ligated into the AccI site of the polylinker of a modified Bluescript SK plasmid. The bluescript borne gene for conferring ampicillin resistance (within the ScaI site) was inactivated by the insertion of a cartridge encoding kanamycin resistance ($Kan^r$, [8]). Synechococcus sp. train PCC 7942 cells were transfected with the library [12]. Single crossover events which conferred $Kan^r$ led to inactivation of various genes. The $Kan^r$ cells were exposed to low $CO_2$ conditions for 8 hours for adaptation, followed by an ampicillin treatment (400 μg/mL) for 12 hours. Cells capable of adapting to low $CO_2$ and thus able to grow under these conditions were eliminated by this treatment. The high-$CO_2$-requiring mutant, IL-2, unable to divide under low $CO_2$ conditions, survived, and was rescued following the removal of ampicillin and growth in the presence of high $CO_2$ concentration.

Cloning of the relevant impaired genomic region from mutant IL-2:

DNA isolated from the mutant was digested with ApaI located on one side of the AccI site in the polylinker; with BamHI or EcoRI, located on the other side of the AccI site; or with MfeI that does not cleave the vector or the $Kan^r$ cartridge. These enzymes also cleaved the genomic DNA. The digested DNA was self-ligated followed by transfection of competent E. coli cells (strain DH5α). $Kan^r$ colonies carrying the vector sequences bearing the origin of replication, the $Kan^r$ cartridge and part of the inactivated gene were then isolated. This procedure was used to clone the flanking regions on both sides of the vector inserted into the mutant. A 1.3 Kbp ApaI and a 0.8 Kbp BamHI fragments isolated from the plasmids (one ApaI site and BamHI site originated from the vector's polylinker) were used as probes to identify the relevant clones in an EMBL3 genomic library of a wild type genome, and for Southern analyses. The location of these fragments in the wild type genome (SEQ ID NO:1) is schematically shown in FIG. 1. The ApaI fragment is between positions 1600 to 2899 (SEQ ID NO:1), marked as T and A in FIG. 1; the BamHI fragment is between positions 4125 to 4957 (SEQ ID NO:1) marked as R and T in FIG. 1. The 0.8 Kbp BamHI fragment hybridized with the 1.6 Kbp HincII fragment (marked E3 in FIG. 1). The 1.3 Kbp ApaI fragment hybridized with an EcoRI fragment of about 6 Kbp. Interestingly, this fragment could not be cloned from the genomic library into E. coli. Therefore, the BamHI site was used (position 2348, SEQ ID NO:1, FIG. 1) to split the EMBL3 clone into two clonable fragments of 4.0 and 1.8 Kbp (E1 and E2, respectively, E1 starts from a Sau3A site upstream of the HindIII site positioned at the beginning of FIG. 1). Confirmation that these three fragments were indeed located as shown in FIG. 1 was obtained by PCR using wild type DNA as template, leading to the synthesis of fragments P1 and P2 (FIG. 1). Sequence analyses enabled comparison of the relevant region in IL-2 with the corresponding sequence in the wild-type.

Experimental Results

Physiological analysis:

The IL-2 mutant grew nearly the same as the wild type cells in the presence of high $CO_2$ concentration but was unable to grow under low $CO_2$. Analysis of the photosynthetic rate as a function of external Ci concentration revealed that the apparent photosynthetic affinity of the IL-2 mutant was 20 mM Ci, which is about 100 times higher than the concentration of Ci at the low $CO_2$ conditions. The curves relating to the photosynthetic rate as a function of Ci concentration, in IL-2, were similar to those obtained with other high-$CO_2$-requiring mutants of Synechococcus PCC 7942 [16, 17]. These data suggested that the inability of IL-2 to grow under low $CO_2$ is due to the poor photosynthetic performance of this mutant.

High-$CO_2$-requiring mutants showing such characteristics were recognized among mutants bearing aberrant carboxysomes [9, 10, 12, 18, 19] or defective in energization of Ci uptake [20, 21]. All the carboxysome-defective mutants characterized to date were able to accumulate Ci within the cells similarly to wild type cells. However, they were unable to utilize it efficiently in photosynthesis due to low activation state of rubisco in mutant cells exposed to low $CO_2$ [10]. This was not the case for mutant IL-2 which possessed normal carboxysomes but exhibited impaired $HCO_3^-$ uptake (Table 1, FIGS. 4a–b). Measurements of $^{14}Ci$ accumulation indicated that $HCO_3^-$ and $CO_2$ uptake were similar in the high-$CO_2$-grown wild type and the mutant (Table 1).

TABLE 1

|  | $CO_2$ Uptake | | $HCO_3^-$ Uptake | |
| --- | --- | --- | --- | --- |
|  | High $CO_2$ | Low $CO_2$ | High $CO_2$ | Low $CO_2$ |
| WT | 31.6 | 53.9 | 30.9 | 182.0 |
| IL-2 | 26.6 | 39.2 | 32.2 | 61.1 |

The rate of $CO_2$ and of $HCO_3^-$ uptake in Synechococcus sp. PCC 79 and mutant IL-2 as affected by the concentration of $CO_2$ in the growth medium. The unidirectional $CO_2$ or $HCO_3^-$ uptake of cells grown under high $CO_2$ conditions or exposed to low $CO_2$ for 12 hours is presented in μmole Ci accumulated within the cells $mg^{-1}$ Chl $h^{-1}$. The results presented are the average of three different experiments, with four replicas in each experiment, the range of the data was within ±10% of the average. WT—wild type.

Uptake of $HCO_3^-$ by wild type cells increased by approximately 6-fold following exposure to low $CO_2$ conditions for 12 hours. On the other hand, the same treatment resulted in only up to a 2-fold increase in $HCO_3^-$ uptake for the IL-2 mutant. Uptake of $CO_2$ increased by approximately 50% for both the wild type and the IL-2 mutant following transfer from high- to low $CO_2$ conditions. These data indicate that $HCO_3^-$ transport and not $CO_2$ uptake was impaired in mutant IL-2.

Figure 4A:
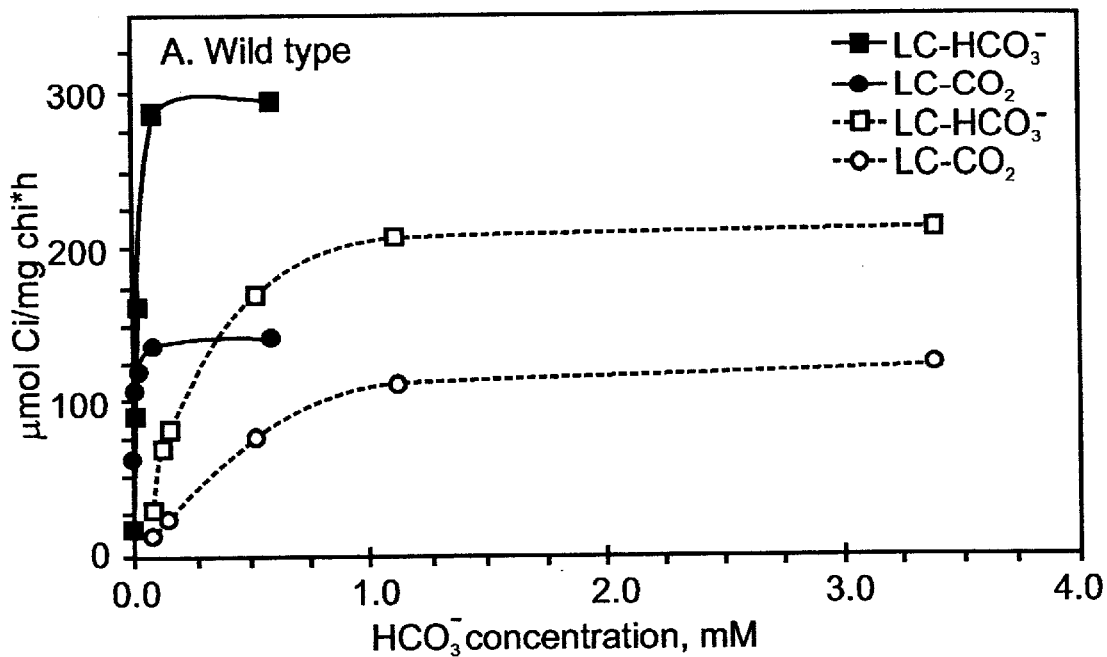
FIGS. 4a–b are graphs showing the rates of $CO_2$ and of $HCO_3^-$ uptake by Synechococcus PCC 7942 (2a) and mutant IL-2 (2b) as a function of external Ci concentration. The rates were assessed from measurements during steady state photosynthesis using a membrane inlet mass spectrometer (MIMS) [6, 7, 22].
Figure 4B:
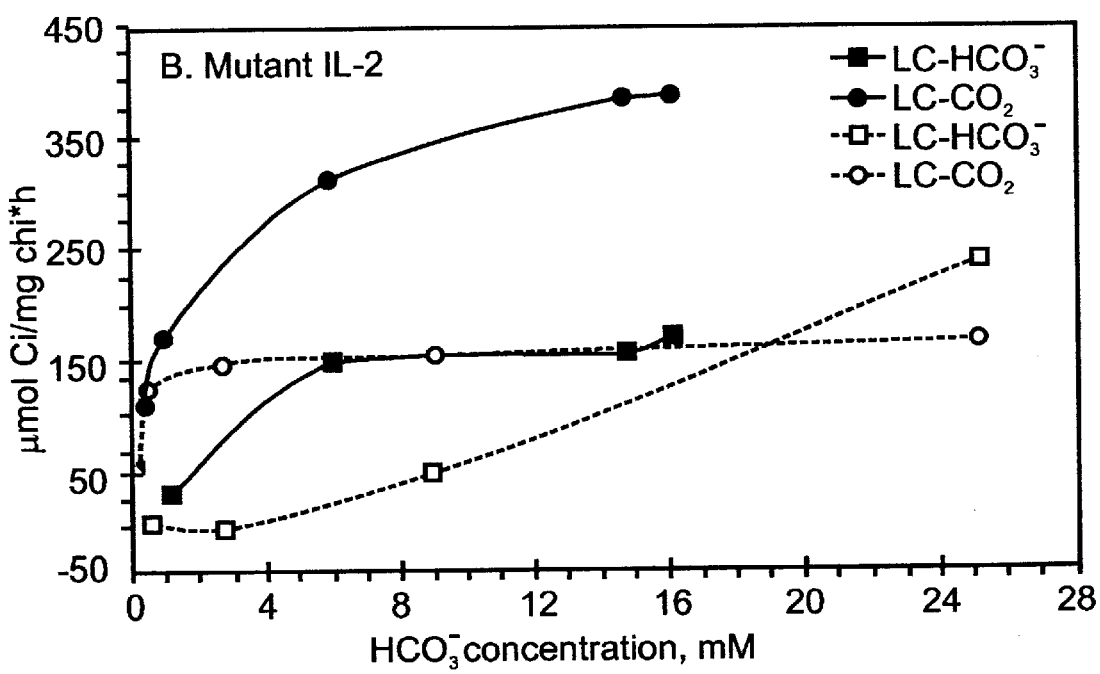

The $V_{max}$ of $HCO_3^-$ uptake, estimated by MIMS [7, 22] at steady state photosynthesis (FIG. 4a), were 220 and 290 μmol $HCO_3^-$ $mg^{-1}$ Chl $h^{-1}$ for high- and low-$CO_2$-grown wild type, respectively, and the corresponding $K_{1/2}$ ($HCO_3^-$) were 0.3 and 0.04 mM $HCO_3^-$, respectively. These estimates are in close agreement with those reported earlier [7]. In high-$CO_2$-grown mutant IL-2, on the other hand, the $HCO_3^-$ transporting system was apparently inactive. The curve relating the rate of $HCO_3^-$ transport as a function of its concentration did not resemble the expected saturable kinetics (observed for the wild type), but was closer to a linear dependence as expected in a diffusion mediated process (FIG. 4b). It was essential to raise the concentration of $HCO_3^-$ in the medium to values as high as 25 mM in order to achieve rates of $HCO_3^-$ uptake similar to the $V_{max}$ depicted by the wild type.

The estimated $V_{max}$ of $CO_2$ uptake by high-$CO_2$-grown wild type and IL-2 was similar for both at around 130–150 $\mu$mol $CO_2$ mg$^{-1}$ Chl h$^{-1}$ and the $K_{1/2}$ ($CO_2$) values were around 5 $\mu$M (FIGS. 4a–b), indicating that $CO_2$ uptake was far less affected by the mutation in IL-2. Mutant cells that were exposed to low $CO_2$ for 12 hours showed saturable kinetics for $HCO_3^-$ uptake suggesting the involvement of a carrier. However, the $K_{1/2}$ ($HCO_3^-$) was 4.5 mM $HCO_3^-$ (i.e., 15- and 100-fold lower than in high- and in low-$CO_2$-grown wild type, respectively) and the $V_{max}$ was approximately 200 $\mu$mol $HCO_3^-$ mg$^{-1}$ Chl h$^{-1}$. These data indicate the presence of a low affinity $HCO_3^-$ transporter that is activated or utilized following inactivation of a high affinity $HCO_3^-$ uptake in the mutant. The activity of the low affinity transporter resulted in the saturable transport kinetics observed in the low-$CO_2$-exposed mutant. These data further demonstrated that the mutant was able to respond to the low $CO_2$ signal.

The reason for the discrepancy between the data obtained by the two methods used, with respect to $HCO_3^-$ uptake in wild type and mutant cells grown under high-$CO_2$-conditions, is not fully understood. It might be related to the fact that in the MIMS method $HCO_3^-$ uptake is assessed as the difference between net photosynthesis and $CO_2$ uptake [6, 7, 22]. Therefore, at Ci concentrations below 3 mM, where the mutant did not exhibit net photosynthesis, $HCO_3^-$ uptake was calculated as zero (FIGS. 4a–b). On the other hand, the filtering centrifugation technique, as used herein, measured the unidirectional $HCO_3^-$ transport close to steady state via isotope exchange, which can explain some of the variations in the results. Not withstanding, the data obtained by both methods clearly indicates severe inhibition of $HCO_3^-$ uptake in mutant cells exposed to low $CO_2$. It is interesting to note that while the characteristics Of $HCO_3^-$ uptake changed during acclimation of the mutant to low $CO_2$, $CO_2$ transport was not affected (FIGS. 4a–b). It is thus concluded that the high-$CO_2$-requiring phenotype of IL-2 is generated by the mutation of a $HCO_3^-$ transporter rather than in non-acclimation to low $CO_2$.

Genomic analysis:

Since IL-2 is impaired in $HCO_3^-$ transport, it was used to identify and clone the relevant genomic region involved in the high affinity $HCO_3^-$ uptake. FIG. 1 presents a schematic map of the genomic region in Synechococcus sp. PCC 7942 where the insertion of the inactivating vector by a single cross over recombination event (indicated by a star) generated the IL-2 mutant. Sequence analysis (GenBank, accession No. U62616, SEQ ID NO:1) identified several open reading frames (identified in the legend of FIG. 1), some are similar to those identified in Synechocystis PCC 6803 [23]. Comparison of the DNA sequence in the wild type with those in the two repeated regions (due to the single cross over) in mutant IL-2, identified several alterations in the latter. This included a deletion of 4 nucleotides in the ApaI side and a deletion of 6 nucleotides but the addition of one bp in the BamHI side (FIG. 5). The reason(s) for these alterations is not known, but they occurred during the single cross recombination between the genomic DNA and the supercoiled plasmid bearing the insert in the inactivation library. The high-$CO_2$-requiring phenotype of mutant JR12 of Synechococcus sp. PCC 7942 also resulted from deletions of part of the vector and of a genomic region, during a single cross over event, leading to a deficiency in purine biosynthesis under low $CO_2$ [24].

The alterations depicted in FIG. 5 resulted in frame shifts which led to inactivation of both copies of ORF467 (nucleotides 2670–4073 of SEQ ID NO:1, SEQ ID NO:2) in IL-2. Insertion of a Kan$^r$ cartridge within the EcoRV or NheI sites in ORF467, positions 2919 and 3897 (SEQ ID NO:1), respectively (indicated by the triangles in FIG. 1), resulted in mutants capable of growing in the presence of kanamycin under low $CO_2$ conditions, though significantly (about 50%) slower than the wild type. Southern analyses of these mutants clearly indicated that they were merodiploids, i.e., contained both the wild type and the mutated genomic regions.

FIGS. 2 and 3 show nucleic and amino acid alignments of ictB and slr1515, the most similar sequence to ictB identified in the gene bank, respectively. Note that the identical nucleotides shared between these nucleic acid sequences (FIG. 2) equal 56%, the identical amino acids shared between these amino acid sequences (FIG. 3) equal 47%, the similar amino acids shared between these amino acid sequences (FIG. 3) equal 16%, bringing the total homology therebetween to 63% (FIG. 3). When analyzed without the transmembrane domains, the identical amino acids shared between these amino acid sequences equal 40%, the similar amino acids shared between these amino acid sequences equal 12%, bringing the total homology therebetween to 52%.

$HCO_3^-$ transporters in Synechococcus sp. PCC 7942:

The protein encoded by ORF467 (SEQ ID NO:3) contains 10 putative transmembrane regions and is a membrane integrated protein. It is somewhat homologous to several oxidation-reduction proteins including the Na$^+$/pantothenate symporter of E. coli (Accession No. P16256). Na$^+$ ions are essential for $HCO_3^-$ uptake in cyanobacteria and the possible involvement of a Na$^+$/$HCO_3^-$ symport has been discussed [3, 25, 26]. The sequence of the fourth transmembrane domain contains a region which is similar to the DCCD binding motif in subunit C of ATP synthase with the exception of the two outermost positions, replaced by conservative changes in ORF467. The large number of transport proteins that are homologous to the gene product of ORF467 also suggest that it is also a transport protein, possibly involved in $HCO_3^-$ uptake. ORF467 is referred to herein as ictB (for inorganic carbon transport B [27]).

Sequence similarity between cmpA, encoding a 42-kDa polypeptide which accumulates in the cytoplasmic-membrane of low-$CO_2$-exposed Synechococcus PCC 7942 [28], and nrtA involved in nitrate transport [29], raised the possibility that CmpA may be the periplasmic part of an ABC-type transporter engaged in $HCO_3^-$ transport [21, Omata, personal communication]. The role of the 42 kDa polypeptide, however, is not clear since inactivation of cmpA did not affect the ability of Synechococcus PCC7942 [30] and Synechocystis PCC6803 [21] to grow under a normal air level of $CO_2$ but growth was decreased under 20 ppm $CO_2$ in air [21]. It is possible that Synechococcus sp. PCC 7942 contains three different $HCO_3^-$ carriers: the one encoded by cmpA; IctB; and the one expressed in mutant IL-2 cells exposed to low $CO_2$ whose identity is yet to be elucidated. These transporters enable the cell to maintain inorganic carbon supply under various environmental conditions.

Transgenic plants transformed with ictB:

The coding region of ictB was cloned downstream of a strong promoter (CaMV 35S) and down stream to and in frame with the transit peptide of pea rubisco small subunit within a plasmid bearing a gene encoding kanamycin resistance, and suitable for the Agrobacterium mediated transformation of Arabidopsis. Transformation of Arabidopsis with this construct resulted in fast growing transgenic plants which were kanamycin resistant. Northern analysis performed on wild type and three transgenic plants (FIG. 6) demonstrated that the transformants expressed the ictB whereas, as expected, the wild type did not.

Measurements of the photosynthetic rate with the aid of a gas exchange system indicated a considerably faster $CO_2$ fixation in the transgenic plants (Table 2). The improved rate of $CO_2$ fixation was mainly pronounced under low $CO_2$ concentrations such as experienced within the air spaces in the leaves of crop plants under most environmental conditions. At higher $CO_2$ concentrations, where the rate of photosynthesis is $CO_2$-saturated and presumably independent of $HCO_3^-$ transport, the wild type and transgenic plants exhibited similar photosynthetic rate, as expected. In a typical air space where the $CO_2$ concentration is 200–300 ppm, the photosynthetic rate of the transgenic plant as 24 to 42% higher than in the wild type. At lower $CO_2$ concentrations such as effectively expected under water-limiting conditions the superiority of the transgenic plant was even more pronounced (Table 2).

TABLE 2

| $CO_2$ Concentration (ppm) | Photosynthetic rate Wild Type ($\mu$mole $CO_2$ m$^{-2}$ s$^{-1}$) | Photosynthetic rate Transgenic plant ($\mu$mole $CO_2$ m$^{-2}$ s$^{-1}$) | Transgenic plant/ Wild Type |
|---|---|---|---|
| 50  | 0.86 | 1.35 | 1.57 |
| 100 | 1.72 | 2.7  | 1.57 |
| 150 | 2.58 | 3.69 | 1.43 |
| 200 | 3.2  | 4.55 | 1.42 |
| 250 | 3.93 | 5.17 | 1.31 |
| 300 | 4.67 | 5.78 | 1.24 |
| 400 | 5.78 | 6.52 | 1.13 |
| 500 | 6.64 | 6.89 | 1.04 |
| 600 | 6.89 | 7.01 | 1.02 |

A comparison of the photosynthetic rate between the wild type and transgenic plants conducted with the aid of a $CO_2$ gas exchange analyzer (ADC, UK, Model LCA-2, Gas Exchange Unit).

It is thus expected that transgenic C3 plants, such as, but not limited to, tobacco, tomato, soybeans, potato, cucumber, cotton, wheat, rice, barley and other C3 and also C4 crop plants, such as corn, sugar cane, sohrgum and others, expressing ictB will grow faster, and produce higher crop yield, including, for example, more and heavier fruits, especially under $CO_2$ and/or water limiting conditions. Tissue specific promoters, such as leaf specific promoters, could be used to highly express the ictB gene in leaves which are the primary photosynthetic organs in most plants.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES

1. Kaplan, A., Schwarz, R., Lieman-Hurwitz, J. and Reinhold, L. (1991) Plant Physiol. 97, 851–855.
2. Badger, M. R. and Price, D. G. (1994) Ann. Rev. Plant Physiol. Plant Mol. Biol. 45, 369–399.
3. Kaplan, A., Schwarz, R., Lieman-Hurwitz, J., Ronen-Tarazi, M. and Reinhold, L. (1994) in: The Molecular Biology of the Cyanobacteria (Bryant, D. Ed.), pp. 469–485, Kluwer Academic Pub., Dordrecht, The Netherlands.
4. Ronen-Tarazi, M., Schwarz, R., Bouevitch, A., Lieman-Hurwitz, J., Erez, J. and Kaplan, A. (1995) in: Molecular Ecology of Aquatic Microbes (Joint, I., Ed.), pp. 323–334. Springer-Verlag, Berlin.
5. Kaplan, A., Ronen-Tarazi, M., Zer, H., Schwarz, R., Tchernov, D., Bonfil, D. J., Schatz, D., Vardi, A., Hassidim, M. and Reinhold, L. (1998) Can. J. Bot. special issue, (In Press).
6. Sultemeyer, D., Price, G. D., Bryant, D. A. and Badger, M. R. (1997) Planta 201, 36–42.
7. Sultemeyer, D., Klughammer, B., Badger, M. R. and Price, G. D. (1998) Plant Physiol. 116, 183–192.
8. Ronen-Tarazi, M., Shinder, V. and Kaplan, A. (1998) FEMS Microbiol Lett. 159, 317–324.
9. Sambrook, J., Fritsch, E. F. and Maniatis, T. (1989) Molecular Cloning. A Laboratory Manual. Cold Spring Harbor Laboratory Press, Cold Spring Harbor, N.Y.
10. Kaplan, A., Marcus, Y. and Reinhold, L. (1988) in: Methods in Enzymology (Packer, L. and Glazer, A. N., Eds.), pp. 534–539. Academic Press, New York.
11. Tchernov, D., Hassidim, M., Luz, B., Sukenik, A., Reinhold, L. and Kaplan, A. (1997) Curr. Biol. 7, 723–728.
12. Badger, M. R. and Price, G. D. (1992) Physiol. Plant. 84, 606–615.
13. Ronen-Tarazi, M., Lieman-Hurwitz, J., Gabay, C., Orus, M. and Kaplan, A. (1995) Plant Physiol. 108, 1461–1469.
14. Dolganov, N. and Grossman, A. (1993) J. Bacteriol. 175, 7644–7651.
15. Ronen-Tarazi, M., Bonfil, D. J., Schatz, D. and Kaplan, A. (1998) Can. J. Bot. special issue, (In Press).
16. Marcus, Y., Schwarz, R., Friedberg, D. and Kaplan, A. (1986) Plant Physiol. 82, 610–612.
17. Schwarz, R., Friedberg, D., Reinhold, L. and Kaplan, A. (1988) Plant Physiol. 88, 284–288.
18. Fukuzawa, H., Suzuki, E., Komukai, Y. and Miyachi, S. (1992) Proc. Natl. Acad. Sci. USA 89, 4437–4441.
19. Schwarz, R., Reinhold, L. and Kaplan, A. (1995) Plant Physiol. 108, 183–190.
20. Marco, M., Ohad, N., Schwarz, R., Lieman-Hurwitz, J., Gabay, C. and Kaplan, A. (1993) Plant Physiol. 101, 1047–1053.
21. Ohkawa, H., Sonoda, M., Katob, H. and Ogawa, T. (1998) in: Proceedings of The Third International Symposium on Inorganic Carbon Uptake by Aquatic Photosynthetic Organisms (Colman, B. Ed.), Can J Bot (in press).
22. Yu, J. W., Price, G. D. and Badger, M. R. (1994) Aust. J. Plant Physiol. 21, 185–195.
23. Kaneko, T., Sato, S., Kotani, H., Tanaka, A., Asamizu, E., Nakamura, Y., Miyajima, N., Hirosawa, M., Sugiura, M., Sasamoto, S., Kimura, T., Hosouchi, T., Matsuno, A., Muraki, A., Nakazaki, N., Naruo, K., Okumura, S., Shimpo, S., Takeuchi, C., Wada, T., Watanabe, A., Yamada, M., Yasuda, M. and Tabata, S. (1996) DNA Res. 3, 109–136.
24. Lieman-Hurwitz J., Schwarz, R., Martinez, F., Maor, Z., Reinhold, L., and Kaplan, A. (1990) in: Proceedings of The Second International Symposium on Inorganic Carbon Uptake by Aquatic Photosynthetic Organisms (Colman, B. Ed.), Can J Bot 69: 945–950.
25. Kaplan, A., Schwarz, R., Ariel, R., and Reinhold, L. (1990) in: Regulation of Photosynthetic Processes (Kanay, R., Katob, R. S. and Miyachi, S. Eds.), Special Issue of the Botanical Magazine, vol. 2, pp. 53–71, Tokyo.

26. Tyrrell, P. N., Kandasamy, R. A., Crotty, C. M. and Espie, G. S. (1996) Plant Physiol. 112, 79–88.
27. Ogawa, T. (1991) Plant Physiol. 96, 280–284.
28. Omata, T. and Ogawa, T. (1986) Plant Physiol. 80, 525–530.
29. Omata, T. (1992) in: Research in Photosynthesis (Murata, N. Ed.) vol. III, 807–810, Kluwer Academic Pub., Dodrecht, The Netherlands.
30. Omata, T., Carlson, T. J., Ogawa, T. and Pierce, J. (1990) Plant Physiol. 93, 305–311.

What is claimed is:

1. A method of enhancing inorganic carbon fixation by a photosynthetic plant, the method comprising the step of transforming cells of the photosynthetic plant with an expressible polynucleotide encoding a polypeptide as set forth in SEQ ID NO:3, said polypeptide enhancing by at least 5% inorganic carbon fixation as compared to, otherwise similar, non-transformed cells of the photosynthetic plant, said polynucleotide comprises a plant promoter operable in expressing said polypeptide.

2. The method of claim 1, wherein said step of transforming said cells of the photosynthetic plant with said expressible polynucleotide is effected by a method selected from the group consisting of genetic transformation and transient transformation.

3. The method of claim 2, wherein said genetic transformation is effected by a method selected from the group consisting of Agrobaterium mediated transformation, electroporation and particle bombardment.

4. The method of claim 2, wherein said transient transformation is effected by a method selected from the group consisting of viral transformation, electroporation and particle bombardment.

5. The method of claim 1, wherein said photosynthetic plant is a C3 plant.

6. The method of claim 5, wherein said C3 plant is selected from the group consisting of tobacco, tomato, soybeans, potato, cucumber, cotton, wheat, rice and barley.

7. The method of claim 1, wherein said photosynthetic plant is a C4 plant.

8. The method of claim 7, wherein said C4 plant is selected from the group consisting of corn, sugar cane and sorghum.

9. The method of claim 1, wherein said plant promoter is selected from the group consisting of a constitutive plant promoter, a tissue specific plant promoter and an inducible plant promoter.

10. The method of claim 9, wherein:
  (i) said constitutive plant promoter is selected from the group consisting of CaMV35S plant promoter, CaMV19S plant promoter, FMV34S plant promoter, sugarcane bacilliform badnavirus plant promoter, CsVMV plant promoter, Arabidopsis ACT2/ACT8 actin plant promoter, Arabidopsis ubiquitin UBQ1 plant promoter, barley leaf thionin BTH6 plant promoter, and rice actin plant promoter;
  (ii) said tissue specific plant promoter is selected from the group consisting of bean phaseolin storage protein plant promoter, DLEC plant promoter, PHSβ plant promoter, zein storage protein plant promoter, conglutin gamma plant promoter from soybean, AT2S1 gene plant promoter, ACT11 actin plant promoter from Arabidopsis, napA plant promoter from *Brassica napus* and potato patatin gene plant promoter; and
  (iii) said inducible plant promoter is selected from the group consisting of a light-inducible plant promoter derived from the pea rbcS gene, a plant promoter from the alfalfa rbcS gene, DRE, MYC and MYB plant promoters which are active in drought; INT, INPS, prxEa, Ha hsp17.7G4 and RD21 plant promoters active in high salinity and osmotic stress, and hsr203J and str246C plant promoters active in pathogenic stress.

11. The method of claim 1, wherein said polynucleotide further comprises a sequence element selected from the group consisting of a nucleic acid sequence encoding a transit peptide, an origin of replication for propagation in bacterial cells, at least one sequence element for integration into a plant's genome, a polyadenylation recognition sequence, a transcription termination signal, a sequence encoding a translation start site, a sequence encoding a translation stop site, plant RNA virus derived sequences, plant DNA virus derived sequences, tumor inducing (Ti) plasmid derived sequences and a transposable element derived sequence.

12. The method of claim 1, wherein said polynucleotide comprises SEQ ID NO:2.

13. An isolated recombinant nucleic acid molecule for enhancing inorganic carbon fixation by a photosynthetic plant, the nucleic acid molecule comprising:
  (a) a polynucleotide encoding a polypeptide as set forth in SEQ ID NO:3; and
  (b) a plant promoter being upstream to said polynucleotide effective in expressing said polypeptide in a plant via nuclear transcription;
with the provision that when said polypeptide is expressed in cells of the photosynthetic plant, at least 5% enhanced inorganic carbon fixation is measurable as compared to otherwise similar, non-transformed, cells of the photosynthetic plant.

14. The isolated nucleic acid molecule of claim 13, wherein said plant promoter is selected from the group consisting of a constitutive plant promoter, a tissue specific plant promoter and an inducible plant promoter.

15. The isolated nucleic acid molecule of claim 14, wherein:
  (i) said constitutive plant promoter is selected from the group consisting of CaMV35S plant promoter, CaMV19S plant promoter, FMV34S plant promoter, sugarcane bacilliform badnavirus plant promoter, CsVMV plant promoter, Arabidopsis ACT2/ACT8 actin plant promoter, Arabidopsis ubiquitin UBQ1 plant promoter, barley leaf thionin BTH6 plant promoter, and rice actin plant promoter;
  (ii) said tissue specific plant promoter is selected from the group consisting of bean phaseolin storage protein plant promoter, DLEC plant promoter, PHSβ plant promoter, zein storage protein plant promoter, conglutin gamma plant promoter from soybean, AT2S1 gene plant promoter, ACT11 actin plant promoter from Arabidopsis, napA plant promoter from *Brassica napus* and potato patatin gene plant promoter; and
  (iii) said inducible plant promoter is selected from the group consisting of a light-inducible plant promoter derived from the pea rbcS gene, a plant promoter from the alfalfa rbcS gene, DRE, MYC and MYB plant promoters which are active in drought; INT, INPS, prxEa, Ha hsp17.7G4 and RD21 plant promoters active in high salinity and osmotic stress, and hsr203J and str246C plant promoters active in pathogenic stress.

16. The isolated nucleic acid molecule of claim 13, further comprising a sequence element selected from the group consisting of an origin of replication for propagation in bacterial cells, at least one sequence element for integration into a plant's genome, a polyadenylation recognition sequence, a transcription termination signal, a sequence encoding a translation start site, a sequence encoding a translation stop site, plant RNA virus derived sequences, plant DNA virus derived sequences, tumor inducing (Ti) plasmid derived sequences and a transposable element derived sequence.

17. A transformed photosynthetic plant comprising the nucleic acid molecule of claim 13.

18. The transformed photosynthetic plant of claim 17, wherein said plant is a C3 plant.

19. The transformed photosynthetic plant of claim 18, wherein said C3 plant is selected from the group consisting of tobacco, tomato, soybeans, potato, cucumber, cotton, wheat, rice and barley.

20. The transformed photosynthetic plant of claim 17, wherein said plant is a C4 plant.

21. The transformed photosynthetic plant of claim 20, wherein said C4 plant is selected from the group consisting of corn, sugar cane and sorghum.

22. The transformed photosynthetic plant of claim 17, wherein said plant is characterized by a photosynthetic rate at least 10% higher as compared to a control non-transformed plant under otherwise identical conditions.

23. The isolated nucleic acid molecule of claim 13, wherein said polynucleotide comprises SEQ ID NO:2.

* * * * *